US006833130B1

(12) United States Patent
Paton et al.

(10) Patent No.: US 6,833,130 B1
(45) Date of Patent: Dec. 21, 2004

(54) RECOMBINANT MICROORGANISMS EXPRESSING AN OLIGOSACCHARIDE RECEPTOR MIMIC

(75) Inventors: Adrienne W. Paton, North Adelaide (AU); Renato Morona, Adelaide (AU); James C. Paton, North Adelaide (AU)

(73) Assignees: Women's and Children's Hospital, North Adelaide (AU); Adelaide Research & Innovation Pty. Ltd., Adelaide (AU)

( * ) Notice: Subject to any disclaimer, the term of this patent is extended or adjusted under 35 U.S.C. 154(b) by 0 days.

(21) Appl. No.: 09/658,537

(22) Filed: Sep. 9, 2000

(30) Foreign Application Priority Data

Sep. 10, 1999 (AU) ............................................ PQ2757

(51) Int. Cl.[7] ............................................ A01N 63/00

(52) U.S. Cl. .................. 424/93.48; 424/93.2; 424/93.4; 435/471; 435/488; 435/243; 435/252.1; 435/252.3; 435/252.33; 435/252.8

(58) Field of Search ............................ 424/93.2, 93.49, 424/3.48, 93.21, 93.4, 93.48, 93.46, 93.42, 93.5, 93.51, 93.6; 435/471, 488, 243, 252.1, 252.3, 252.33, 252.8, 320.1, 235.1, 262; 514/44

(56) References Cited

U.S. PATENT DOCUMENTS

| | | | | |
|---|---|---|---|---|
| 4,698,332 | A | 10/1987 | Ogasawara et al. | 514/42 |
| 5,032,519 | A | 7/1991 | Paulson et al. | 435/193 |
| 5,089,479 | A | 2/1992 | Krivan et al. | 514/25 |
| 5,260,380 | A | 11/1993 | Isayev et al. | 525/177 |
| 5,401,723 | A | 3/1995 | Gaffar et al. | 514/21 |
| 5,514,660 | A | 5/1996 | Zopf et al. | 514/25 |
| 5,576,305 | A | 11/1996 | Ratcliffe | 514/25 |
| 5,614,374 | A | 3/1997 | Adachi et al. | 435/26 |
| 5,627,163 | A | 5/1997 | Heerze et al. | 514/61 |
| 5,696,000 | A | 12/1997 | Krivan et al. | 435/732 |
| 5,736,533 | A | 4/1998 | Simon et al. | 514/61 |
| 5,753,631 | A | 5/1998 | Paulson et al. | 514/25 |
| 5,811,404 | A | 9/1998 | DeFrees et al. | 514/25 |
| 5,849,714 | A | 12/1998 | Rafter et al. | 514/23 |
| 5,955,347 | A | 9/1999 | Lowe | 475/252.3 |
| 6,069,137 | A | 5/2000 | Heerze et al. | 514/61 |

FOREIGN PATENT DOCUMENTS

| | | | |
|---|---|---|---|
| EP | WO 95/33467 | A2 | 12/1995 |
| EP | WO 96/40169 | A1 | 12/1996 |
| EP | WO 97/03701 | A2 | 2/1997 |
| EP | WO 98/14215 | A2 | 4/1998 |
| EP | WO 99/56754 | A1 | 11/1999 |
| JP | 2268129 | | 1/1990 |
| JP | 7258093 | A | 10/1995 |
| JP | 9315981 | A | 12/1997 |
| JP | 10-029945 | A | 2/1998 |

OTHER PUBLICATIONS

AW Paton et al. Nature Medicine, "A new biological agent for treatment of Shiga toxigenic *Escherichia coli* infections and dysentery in humans," Mar. 2000, vol. 6, No. 3, pp. 265–270.*

JT Ngo et al., The Protein Folding Problem and Tertiary Structure Prediction, "Computational Complexity, Protein Structure Prediction, and the Levinthal Paradox," 1994, pp. 491–494.*

T–L Chiu et al., Folding & Design, "Optimizing energy potentials for success in protein tertiary structure prediction," May 1998, 3: pp. 223–228.*

CA Brackelsberg et al., Vet Res Commun, "Characterization of *Salmonella dublin* and *Salmonella typhimurium* (Coopenhagen) isolates from cattle," Aug. 1997, 21(6):409–420, Abstract.*

U Kues et al., Microbiol Rev, "Replication of plamids in gram–negative bacteria," Dec. 1989, 53(4):491–516, Abstract.*

DE Heinrichs et al., Journal of Biological Chemistry, "The Assembly System for the Outer Core Portion of R1– and R4–type Lipopolysaccharides of *Escherichia coli,*" 1998, vol. 273, No. 45, pp. 29497–29505.*

M Gilbert et al., Journal of Biological Chemistry, "The Genetic Bases for the Variation in the Lipo–oligosaccharide of the Mucosal Pathogen , *Campylobacter jejuni,*" 2002, vol. 277, No. 1, pp. 327–337.*

S Moriya et al., Plasmid, "Regulation of Initiation of *Bacillus subtillis* Chromosome Replication," 1999, 41: pp. 17–29.*

M Malissard et al., Glycoconjuage Journal, "The yeast expression system for recombinant glycosyltransferases," 1999, 16, pp. 125–139.*

JC Paton et al., Infection and Immunity, "Oral Administration of Formaldehyde–Killed Recombinant Bacteria Expressing a Mimic of the Shiga Toxin Receptor Protects Mice from Fatal Challenge with Shiga–Toxigenic *Escherichia coli,*" Mar. 2001, vol. 69, No. 3, 1389–1393.*

(List continued on next page.)

*Primary Examiner*—Scott D. Priebe
*Assistant Examiner*—Brian Whiteman
(74) *Attorney, Agent, or Firm*—Townsend and Townsend and Crew LLP

(57) ABSTRACT

Chimeric carbohydrates produced by recombinant microorganism carrying exogenous glycosyltransferases act with or without exogenous enzymes required for synthesis or nucleotide synthesis precursors. These recombinant microorganism can be used for competitively inhibiting the binding of toxins or adhesins to receptors of mucosal surfaces, especially gastrointestinal surface. In particular chimeric sugar moieties have been made for lipopolysaccharides, in recombinant microorganism that present multiple copies of the oligosaccharides. The oligosaccharide moieties so presented act as receptor mimic for toxins and adhesins. A number have been synthesized and have been shown to confer protection against attack by pathogenic organisms or their products in vitro and in vivo.

32 Claims, 5 Drawing Sheets

OTHER PUBLICATIONS

CM Krinos et al., Nature, "Extensive surface diversity of a commensal microorganism by multiple DNA inversions," Nov. 2001, vol. 414, pp. 555–558.*

Yazawa et al., Breast Cancer Research and Treatment, vol. 66, pp. 165–170, 2001.*

Argnani et al., Microbiology, vol. 142, pp. 109–114, 1996.*

Takeda, et al. "In Vitro Assessment of a Chemically Synthesized Shiga Toxin Receptor Analog Attached to Chromosorb P (Synsorb Pk) as a Specific Absorbing Agent of Shiga Toxin 1 and 2" *Microbiol. Immunol.* (1999), vol. 43 (4), pp. 331–337.

van Alphen, et al. "Blocking of Fimbria–Mediated Adherence of *Haemophilus influenzae* by Sialyl Gangliosides" *Infection and Immunity* (Dec. 1991) vol. 59(12), pp. 4473–4477.

Willemsen, et al. "Multivalent Binding of K99 Fimbriae to the N–Glycolyly–$GM_3$ Ganglioside Receptor" *Infection and Immunity* (Oct. 1993) vol. 61(10), pp. 4518–4522.

Yan, et al. "Determination of GDP–Fuc: Gal$\beta$1–4GlcNAc–R (Fuc to GlcNAc) $\alpha$ 1,3 Fucosyltransferase Activity by a Solid–Phase Method" *Analytical Biochemistry* (1994) vol. 223, pp. 111–118.

Newburg, David S. "Do the Binding Properties of Oligosaccharides in Milk Protect Human Infants from Gastrointestinal Bacteria" *Symposium: Bioactive Components in Milk and Development of the Neonate: Does Their Absence Make a Difference, presented by The American Society for Nutritional Studies.* (1997) pp. 980S–984S.

Paton, et al. "A New Biological Agent for Treatment of Shiga Toxigenic *Escherichia coli* Infections and Dysentery in Humans" *Nature Medicine* (Mar. 2000) vol. 6(3), pp. 265–270.

Phillips, et al. "Characterization of Chimeric Lipopolysaccharides from *Escherichia coli* Strain JM109 Transformed with Lipooligosaccharide Synthesis Genes (Isg) from *Haemophilus influenzae*" *J. Biol. Chem. USA,* 2000, vol. 257 (7), pp. 4747–4758.

Reyes–Leyva, et al. "The Porcine Paramyxovirus LPM Specifically Recognizes Sialyl (a 2,3) Lactose–containing Structures" *Arch Virol* (1993) vol. 133, pp. 195–200.

Roberts, et al. "Sialic Acid–dependent Adhesion of *Mycoplasma pneumoniae* to Purified Glycoproteins" *J. of Biological Chemistry* (Jun. 1989) vol. 264(16), pp. 9289–9293.

Schwertmann, et al. "S–Fimbriae From *Escherichia coli* Bind to Soluble Glycoproteins From Human Milk" *J. of Pediatric Gastroenterology and Nutrition* (Mar. 1999) vol. 28, pp. 257–263.

Sjöberg, et al. "Purification and Characterization of CS2, a Sialic Acid–specific Haemagglutinin of Enterotoxigenic *Escherichia coli*" *Biochem J.* (1988) vol. 255, pp. 105–111.

Stehle, et al. "Crystal Structures of Murine Polyomavirus in Complex with Straight–chain and Branched–chain Sialyloligosaccharide Receptor Fragments" *Structure* (1996) vol. 4(2), pp. 183–194.

Taiyo, Kaguki "Sialyloligosaccharides from Egg Yolk as an Inhibitor of Rotaviral Infection" *J. Agric. Food Chem.* (1995) vol. 43, pp. 858–861.

Klemm, et al. "A Stochastic Killing System for Biological Containment of *Escherichia coli*" *Applied and Environmental Microbiology* (Feb. 1995), vol. 61(2), pp. 481–486.

Klenk, et al. "Carbohydrate–Mediated Adhesion of Viruses" *Nova Acta Leopoldina NF* (1997) vol. 75(301), pp. 131–142.

Koeller et al. "Tyrosine Sulfation on a PSGL–1 Glycopeptide Influences the Reactivity of Glycosyltransferases Responsible for Synthesis of the Attached O–Glycan" *J. Am. Chem. Soc.* (2000) vol. 122, pp. 742–743.

Krivan, et al. "Many Pulmonary Pathogenic Bacteria Bind Specifically to the Carbohydrate Sequence (GalNAcB1–4Gal) Found in Some Glycolipids" *Proc. Natl. Acad. Sci. USA* (1998) vol. 85 pp. 6157–6161.

Kuo, et al. An N–linked High–mannose Type Oligosaccharide, Expressed at the Major Outer Membrane Protein of *Chlamydia trachomatis,* Mediates Attachment and Infectivity of the Microorganism to HeLa Cells *J. Clin. Invest.* (Dec. 1996) vol. 98(12), pp. 2813–2818.

Lanne, et al. "Enhanced Binding of Enterotoxigenic *Escherichia coli* K99 to Amide Derivatives of the Receptor Ganglioside NeuGc–$GM_3$" *Biochemistry* (1995) vol. 34, pp. 1845–1850.

Levine, et al. "Recombinant DNA Risk Assessment Studies in Humans: Efficacy of Poorly Mobilizable Plasmids in Biologic Containment" *J. of Infectious Diseases* (Oct. 1983), vol. 148(4), pp. 699–709.

Matei, et al. "Isolation of Natural Fucose–containing Saccharides and Preliminary Data on Their Effectiveness in Inhibition of *Candida albicans* Adherence to Human Buccal Epithelial Cell" *Rev. roum. Biochim* (1997) vol. 34, pp. 123–130.

May, et al. "Expression, Crystallization, and Preliminary X–ray Analysis of a Sialic Acid–binding Fragment of Sialoadhesin in the Presence and Absence of Ligand" *Protein Science* (1997) vol. 6, pp. 717–721.

Neeser, et al. "A 23 kDa Membrane Glycoprotein Bearing (NeuNAca2–3GalB1–)3GalNAc O–linked Carbohydrate Chains Acts as a Receptor for *Streptococcus sanguis* Omz 9 on Human Buccal Epithelial Cells" *Glycobiology* (1995) vol. 5(1), pp. 97–104.

Crocker, et al. "The Potential Role of Sialoadhesin as a Macrophage Recognition Molecule in Health and Disease" *Glycoconjugate Journal* (1997) vol. 14, pp. 601–609.

Donnelly, et al. "Blocking Bacterial Entertoxins" *Nature Medicine,* (Mar. 2000), vol. 6 (3), pp. 257–258.

Eisen, et al. "Binding of the Influenza A Virus to Cell–Surface Receptors: Structures of Five Hemagglutinin–Sialyoligosaccharide Complexes Determined by X–ray Crystallography" *Virology* (1997) vol. 232, pp. 19–31.

Falk, et al. "An in vitro Adherence Assay Reveals that *Helicobacter pylori* Exhibits Cell Lineage–specific Tropism in the Human Gastric Epithelium" *Proc. Natl. Acad. Sci. USA* (Mar. 1993) vol. 90, pp. 2035–2039.

Frank, et al. "Comparison of the Conformational Behavior of Sialyllactose Complexed with the two Viral Attachment Proteins Influenza A Hemagglutinin and the Murine Polymavirus" *J. Mol. Model* (1997) vol. 3, pp. 408–414.

Gambaryan, et al. "Specification of Receptor–Binding Phenotypes of Influenza Virus Isolates from Different Hosts Using Synthetic Sialylglycopolymers: Non–Egg–Adapted Human H1 and H3 Influenza A and Influenza B Viruses Share a Common High Binding Affinity for 6' Sialyl–(N–acetyllactosamine)" *Virology* (1997) vol. 232, pp. 345–350.

Herrier, et al. "The Surface Receptor is a Major Determinant of the Cell Tropism of Influenza C Virus" *Virology* (1987) vol. 159, pp. 102–108.

Idänpään–Heikkilä, et al. "Oligosaccharides Interfere with the Establishment and Progression of Experimental Pneumococcal Pneumonia" *J. of Infectious Diseases* (1997) vol. 176, pp. 704–712.

Idota, et al. "Growth–promoting Effects of N–Acetylneuraminic Acid–containing Substances on Bifidobacteria" *Biosci. Biotech. Biochem.* (1994) vol. 58(9), pp. 1720–1722.

Idota, et al. "Inhibition of Cholera Toxin by Human Milk Fractions and Sialyllactose", *Biosci. Biotech. Biochem.* (1995) vol. 59(3) pp. 417–419.

Johnson, et al. "Synthesis of Oligosaccharides by Bacterial Enzymes" *Glycoconjugate Journal,* 1999, vol. 16, pp. 141–146.

Annaix, et al. "Structures Involved in the Binding of Human Fibrinogen to *Candida albicans* Germ Tubes" *FEMS Microbiology Immunology,* (1990) vol. 64, pp. 147–154.

Armstrong, et al. "Clinical Trials of Synsorb–Pk in Preventing Hemolytic–Uremic Syndrome" Kaper O Brien eds *Escherichia coli* O157:H7 and other Shiga Toxin–Producing *E. coli* Strains. American Society for Microbiology, Washington, D.C. (1998) pp. 374–384.

Armstrong, et al. "Investigation of Shiga–like Toxin Binding to Chemically Synthesized Oligosaccharide Sequences" *J. Infect. Dis.* (1991) vol. 164, pp. 1160–1167.

Barra, et al. "*Escherichia coli* Heat–labile Enterotoxin Preferentially Interacts with Blood Group A–active Glycolipids From Pig Intestinal Mucosa and A– and B– active Glycolipids From Human Red Cells Compared to H–active Glycolipids" *Molecular and Cellular Biochemistry,* (1992) vol. 115, pp. 63–70.

Bauer, et al. "Genetic and Structural Analysis of a Virulence Determinant in Polyomavirus VP1" *Journal of Virology* (Dec. 1995) vol. 69(12), pp. 7925–7931.

Bouchara, et al. "Sialic Acid–Dependent Recognition of Laminin and Fibrinogen by *Aspergillus fumigatus* Conidia" *Infection and Immunity* (Jul. 1997), vol. 65(7), pp. 2717–2724.

Brown, et al. "Erythrocyte P Antigen: Cellular Receptor for B19 Parvovirus" *Science* (Oct. 1993) vol. 262, pp. 114–117.

Cameron, et al. "Blood Group Glycolipids as Epithelial Cell Receptors for *Candida albicans*" *Infection and Immunity* (Mar. 1996) vol. 64(3), pp. 891–896.

Cao, et al. "Role of Carbohydrate–mediated Adherence in Cytopathogenic Mechanisms of Acanthamoeba" *The Journal of Biological Chemistry* (Jun. 1998) vol. 273(25), pp. 15838–15845.

Connor, et al. "Receptor Specificity in Human, Avian, and Equine H2 and H3 Influenza Virus Isolates" *Virology* (1994) vol. 205, pp. 17–23.

Critchley, et al. "Role of Glycosides as Epithelial Cell Receptors for *Candida albicans*" *J. of General Microbiology* (1987) vol. 133, pp. 637–643.

* cited by examiner

RECOMBINANT MICROORGANISMS EXPRESSING AN OLIGOSACCHARIDE RECEPTOR MIMIC

FIELD OF THE INVENTION

This invention relates to recombinant microorganisms (i.e., bacteria, yeast, and fungi) that display an oligosaccharide-comprising binding moiety that can compete with a ligand for binding to a receptor for the ligand, and use of the microorganisms to deliver the oligosaccharide to a human or other animal. The microoganism can be used for adsorbing toxins or pathogenic microorganisms from a particular environment.

BACKGROUND OF THE INVENTION

Surfaces of all cells express a complexity of oligosaccharides that provide a number of functions. A primary one of these functions is determining on their own or together with other molecules, interactions with other cells or molecules. The nature, linkage and conformation of sugar residues of the oligosaccharides, and in particular residues at or close to the non-reducing terminus of an oligosaccharide, determines whether the oligosaccharide will or will not participate in a particular receptor-ligand interaction.

The susceptibility of an animal to infection and the eventual physiological site affected by an infection is to a large extent determined by the expression on the cell surface of such oligosaccharide receptors. In the case of enteric infections, one primary prerequisite for pathogenesis is that the microorganism persists in the intestinal lumen of the host. Generally this requires some form of adherence to the lumeinal epithelium (forming the mucosal surface of the gut), otherwise the micro-organism is flushed from the gut. Additionally for a toxigenic organism, the toxin also needs to bind to the luminal epithelium and, for some toxins, needs to be absorbed systemically to be effective, otherwise, it too would be flushed from the gut.

Certain surface structures of pathogenic and other bacteria known as adhesins mediate adherence to luminal epithelial cells. A number of adhesins are known and organisms without adhesins are generally of low virulence. Adhesins are proteinaceous factors which promote the adherence of bacteria and viruses to cells of their hosts. Adhesins can be either fimbrial or filamentous in structure or they may be afimbrial. Adhesins associated with fimbriae may be associated with accessory proteins such as tip proteins at an extreme end of the fimbrial structure and such tip proteins can be regarded as lectins. The receptor on the host cell has in some cases been determined and shown to be a carbohydrate such as an oligosaccharide associated with a glycolipid or a glycoprotein.

The best characterised system from a molecular and biological viewpoint, is the P-fimbriae (also called pili) produced by uropathogenic *Escherichia coli*. This tip adhesin binds the glycolipid $Gb_3$ (globotriaosyl ceramide—see below) and the fimbrial subunits can be purified by affinity chromatography using a $Gb_3$ mimic. Another well characterised group of adhesins are those associated with enterotoxigenic *E. coli* (ETEC) strains which infect pigs to cause scours. These are termed the K88 type and a number of variants are known, being K88ab, K88ac and K88ad. The adhesins associated with these fimbriae have been shown to have different receptor requirements, which includes the presence of both glycolipid and protein receptors. The carbohydrate requirement has been characterised in at least some of these, for example K88ad uses carbohydrates of the lactoneotetraose series of glycolipids.

A number of toxins have been identified and include, Shiga toxins (also referred to as Shiga-like toxins and verotoxins), toxins produced by various species of Clostridia, including tetanus toxin, botulinum toxin, and *C. diffcile* toxins A and B, Staphylococcal enterotoxins, *Escherichia coil* heat labile and heat stable enterotoxins and cholera toxin. Without toxin activity the majority of otherwise enterotoxigenic bacteria would be less capable of causing disease.

The receptors for the majority of adhesins and toxins identified to date are carbohydrate in nature. For example, the glycolipid globotriaosyl ceramide ($Gb_3$) which has the structure Galα[1→4]Galβ[1→4]Glc-ceramide, is the preferred receptor for most members of the Shiga toxin family. Similarly, the ganglioside $G_{M1}$ is the receptor for cholera toxin and *E. coli* heat labile enterotoxin type I. *C. difficile* toxin A binds to several host receptors, all of which have in common a Galβ[1→4]GlcNAc moiety. The neurotoxin produced by *C. botulinum* is also believed to be specific for a sialic acid containing glycoprotein or glycolipid present on neurons. The terminal Galα[1→4]Galβ moiety present on $Gb_3$ is the receptor for P pili, the major adhesin of uropathogenic *E. coli* strains. Similarly, asialo-$G_{M1}$ is the receptor for adhesive pili (CFAs) of some enterotoxigenic *E. coli* strains. The sialated gangliosides NeuGc-$GM_3$ and NeuNAc-$GM_3$ have also been identified as the target cell receptors for porcine rotavirus strains, and it is presumed that rotavirus strains causing disease in humans also bind specific oligosaccharide moieties present on cell surface glycolipids.

The elucidation of the nature of oligosaccharides acting as receptors for particular toxins and pathogenic microorganisms has opened up a promising avenue in the diagnosis and potential treatment or prevention of diseases caused by these agents. The use of the sugar residues forming receptors for toxins or adhesins has been proposed as a means of specifically identifying the toxins or bacteria involved in an infection. For example, the ganglioside receptor $G_{M1}$ is used as a specific capturing agent in ELISA assays for the presence of cholera toxin.

It has also been proposed to use synthetically prepared oligosaccharides as a means of adsorbing toxins or the like from samples. Examples of proposed uses of receptors for adsorbing toxins or pathogenic organisms out of a sample include Krivan et al in U.S. Pat. No. 5,696,000 which discusses the pharmaceutical use of certain tetra- and trisaccharide receptors coupled to a carrier such as a liposome to inhibit the adherence of micro-organisms to susceptible cells. A similar use for toxins such as Shiga toxin, can be seen in U.S. Pat. No. 5,849,714 to Rafter et al which discloses the use of a synthetic construct of sugar residues making up the globotriose receptor, coupled by a linker to an inert support for use in treatment of bacterial dysentery.

A problem arises, however, in the synthesis and delivery of these compounds, because oligosaccharides are difficult or expensive to synthesise chemically, the conformation may not be appropriate, and the oligosaccharide may preferably need to be presented in an immobilized (non-diffusible) form. Thus, there is a need to provide a mechanism for delivery and presentation of the oligosaccharide moiety in an appropriate conformation in the environment where the toxin or pathogenic organism is to be adsorbed (for example the gastrointestinal tract).

SUMMARY OF THE INVENTION

The invention provides, in a first embodiment, a recombinant microorganism that displays on its surface a binding moiety that, when administered to an animal, competes with a ligand for binding to a receptor for the ligand. The binding moiety includes an oligosaccharide that is composed of at least one sugar residue that is attached to an acceptor moiety by a glycosyltransferase that is encoded by an exogenous nucleic acid which is present in the microorganism. The oligosaccharide can further include at least a second sugar residue that is attached to the acceptor moiety by at least a second glycosyltransferase. One or more of the additional glycosyltransferases can also be encoded by one or more exogenous nucleic acids that are present in the microorganism.

The receptor is typically present on a surface of a cell. Cells of interest include, for example epithelial or endothelial cells, in particular those that are present in an animal mucosal membrane.

The binding moiety is, in some embodiments, a mimic of a receptor for a toxin or adhesin of a pathogenic organism. Examples of toxins include, but are not limited to, enterotoxins, including shiga toxins, clostridial toxins, cholera toxins, *E. coli* enterotoxins, and Staphylococcal enterotoxins. In other embodiments, the binding moiety is a mimic of an adhesin receptor. Adhesins of interest include, but are not limited to, a CFA adhesin of an enterotoxigenic *E coli., E. coli* CS3 pili, K88ad fimbriae, an adhesin of *Entamoeba histolyticum,* and an adhesin of a virus.

In some embodiments, the binding moiety competes with a pathogenic organism for binding to a corresponding receptor on an animal epithelial or endothelial cell. Pathogenic organisms of interest include, for example, *Staphylococcus pneumonia, H. influenza, H. parainfluenza, Chlamydia trachomatis,* Acanthamoeba, *Candida albicans, Helicobacter pylori* and Pseudomonas spp.

In other embodiments, the binding moiety is a mimic of a receptor for a cell or molecule involved in inflammation. For example, the binding moiety can include a 3'-sialoside or a 6'-sialoside. Sialyl Lewis$^x$ and sialyl Lewis$^a$ are other examples of oligosaccharide structures that can function as a receptor mimic. Microorganisms that display these molecules can compete with leukocytes, for example, for binding to endothelial cells in the vasculature or other tissues and thus inhibit inflammation.

The invention also provides a recombinant microorganism expressing one or more exogenous sugar transferases, or one or more exogenous nucleotide sugar precursor synthesizing enzymes, said microorganism also expressing an acceptor molecule, said one or more exogenous sugar transferases being specific for the transfer of one or more sugar residues represented progressively from a non reducing terminal end of a receptor of either a toxin or an adhesin of a pathogenic organism, the exogenous sugar transferases progressively transferring said one or more sugar resides onto the acceptor molecule to thereby form a chimeric carbohydrate molecule with an exposed receptor mimic, said sugar precursor enzymes forming nucleotide precursors that are transferred to said acceptor molecule to make up said chimeric carbohydrate, said exposed receptor mimic capable of binding the toxin or the adhesin.

Also provided by the invention are preparations for administration to a mucosal surface. The preparations include a delivery microorganism or a partially or fully purified non-toxic preparation of a carbohydrate molecule therefrom. At least a part of the carbohydrate molecule generally acts as an exposed receptor mimic. For example, the receptor mimic can be capable of binding a toxin or an adhesin of a pathogen that normally binds to the mucosal surface. The receptor mimic is generally carried in a pharmaceutically acceptable excipient.

The invention also provides methods of administering a receptor mimic to a mucosal surface of a mammal. The methods involve the administration of a quantity of a delivery microorganism, or parts thereof, the delivery microorganism exhibiting one or more sugars in a configuration to form an exposed receptor mimic, the receptor mimic being a mimic of a receptor of a pathogen, said quantity being sufficient to reduce adherence of the pathogen or a toxin produced by the pathogen to the mucosal surface.

In another embodiment, the invention provides methods of testing for the presence of a toxin or a pathogenic microorganism in a sample. These methods involve, for example, contacting a sample with the purified carbohydrate as described above, with either the purified carbohydrate or the sample being immobilized. Unbound purified carbohydrate or toxin or pathogenic microorganism is washed off, and a detection means is added to detect bound purified carbohydrate and the toxin or pathogenic microorganism.

BRIEF DESCRIPTION OF THE FIGURES

FIG. 1 shows a plot showing the protective efficacy of formaldehyde-killed-receptor mimic bacteria. Groups of six streptomycin-treated mice were challenged with 97MW1, and then treated orally twice or three times daily with *E. coli* CWG308 or CWG308:pJCP-$Gb_3$. The survival time of each mouse is shown.

FIG. 2 shows representations of histological confirmation of STEC-induced renal injury. Kidneys were removed from an uninfected control mouse (A), a CWG308-treated mouse which died four days after challenge with 97MW1 (B), and two different CWG308:pJCP-$Gb_3$ treated mice which were alive and well 12 days after challenge with 97MW1 (C and D). Kidneys were fixed, sectioned and stained with H&E as described the materials and methods of example 2.

FIG. 3 is a plot showing the effect of delayed therapy with CWG308:pJCP-$Gb_3$ on survival of mice challenged with 97MW1. Groups of four mice were challenged with 97MW1 and treatment with CWG308:pJCP-$Gb_3$ was commenced either immediately, after a delay of 8, 16, 24 or 48 hours, or not at all. Survival time of each mouse is indicated.

FIG. 4 is a plot showing the effect of delayed therapy with CWG308:pJCP-$Gb_3$ on survival of mice challenged with 98NK2. Groups of eight mice were challenged with 98K2 and treatment with CWG308:pJCP-$Gb_3$ was commenced either immediately, after a delay of 8, 16, 24 or 48 hours, or not at all. Survival time of each mouse is indicated.

FIG. 5 shows representations of silver stained SDS-PAGE analysis of LPS purified from *E. coli* CW308 derivatives. Lane 1, CWG308; lane 2, CWG308:pJCP-$Gb_3$; lane 2, CWG308:pJCP-lgtCDE; lanes 4 and 5 CWG308:pJCP-lgtCDE/gne (two separate preparations); lane 6 CWG308:pJCP-lgtCDE/wbnF. Each lane contains approximately 3 $\mu$g of LPS.

DETAILED DESCRIPTION OF THE INVENTION

Definitions

The following abbreviations are used herein:

Ara=arabinosyl;

Fru=fructosyl;

Fuc=fucosyl;

Gal=galactosyl;
GalNAc=N-acetylgalactosaminyl;
Glc=glucosyl;
GlcNAc=N-acetylglucosaniinyl;
Man=mannosyl; and
NeuAc or NeuNAc=sialyl (N-acetylneuraminyl).

Typically, sialic acid is 5-N-acetylneuraminic acid, (NeuAc) or 5-N-glycolylneuraminic acid (NeuGc). Other sialic acids may be used in their place, however. For a review of different forms of sialic acid suitable in the present invention see, Schauer, *Methods in Enzymologly,* 50: 64–89 (1987), and Schaur, *Advances in Carbohydrate Chemistry and Biochemistry,* 40: 131–234.

Donor substrates for glycosyltransferases are activated nucleotide sugars. Such activated sugars generally consist of uridine and guanosine diphosphate, and cytidine monophosphate, derivatives of the sugars in which the nucleoside diphosphate or monophosphate serves as a leaving group. Bacterial, plant, and fungal systems can sometimes use other activated nucleotide sugars.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right. All oligosaccharides described herein are described with the name or abbreviation for the non-reducing saccharide (e.g., Gal), followed by the configuration of the glycosidic bond ($\alpha$ or $\beta$), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant nucleic acid" refers to a nucleic acid that was artificially constructed (e.g., formed by linking two naturally-occurring or synthetic nucleic acid fragments). This term also applies to nucleic acids that are produced by replication or transcription of a nucleic acid that was artificially constructed. A "recombinant polypeptide" is expressed by transcription of a recombinant nucleic acid (i.e., a nucleic acid that is not native to the cell or that has been modified from its naturally occurring form), followed by translation of the resulting transcript.

A "heterologous polynucleotide" or a "heterologous nucleic acid", as used herein, is one that originates from a source foreign to the particular host cell, or, if from the same source, is modified from its original form. Thus, a heterologous glycosyltransferase gene in a prokaryotic host cell includes a glycosyltransferase gene that is endogenous to (i.e., naturally present in) the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

The term "isolated" or "purified" is meant to refer to material which is substantially or essentially free from components which otherwise accompany the material in its native state. For the oligosaccharide-containing binding moieties of the invention, for example, a preparation of isolated or purified binding moieties includes a preparation that is substantially free of nucleic acids (e.g., genomic and other nucleic acids that are found in the microorganism cell that synthesized the oligosaccharide). Typically, isolated or purified oligosaccharides, glycoproteins, glycolipids, or other preparations from a recombinant microorganism of the invention are at least about 80% pure, usually at least about 90%, and preferably at least about 95% pure as measured by band intensity on a silver stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized.

Detailed Description

Figure 1:
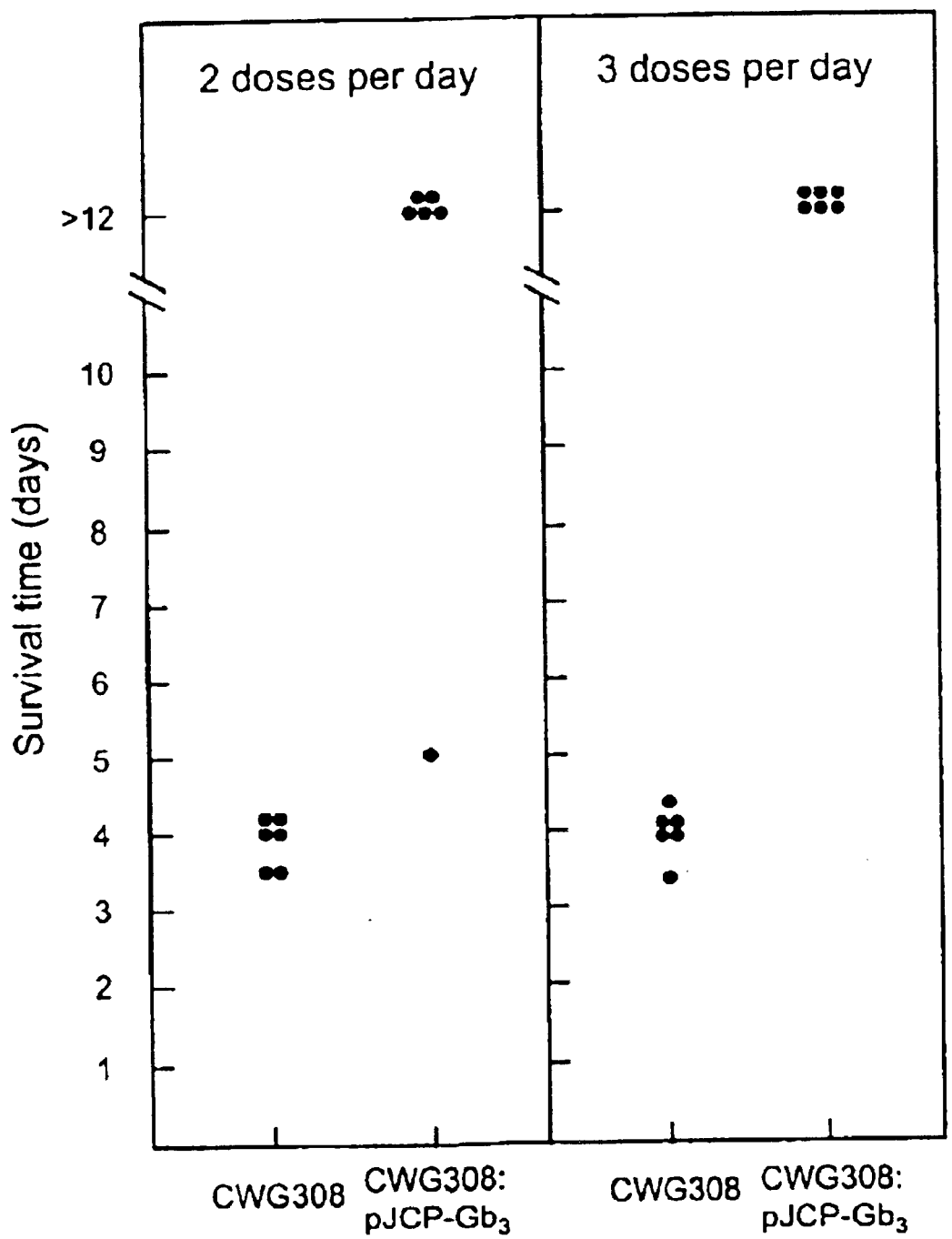

This invention provides recombinant microorganisms that are useful for synthesizing and delivering specific oligosaccharide structures to an organism. The microorganisms synthesize oligosaccharides that, for example, function as a binding moiety that, when administered to an animal, competes with a ligand for binding to a receptor for the ligand. The oligosaccharides are synthesized in situ and displayed on the surface of the microorganism. The oligosaccharide portion of the binding moiety includes one or more sugar residues that are attached to an acceptor moiety by glycosyltransferases. At least one of the glycosyltransferases that are involved in synthesis of the oligosaccharide is encoded by an exogenous nucleic acid which is present in the microorganism.

Upon administration to a human or other animal, the recombinant microorganisms of the invention can function as a delivery vehicle for the surface-displayed oligosaccharides, which are delivered to a target site, such as an endothelial or epithelial tissue, in the animal. The oligosaccharides can then exert an effect, such as binding to a receptor on a cell, thus inhibiting binding of another ligand for the cell (e.g., a bacteria or virus, a toxin, a cell involved in inflammation, etc.). The use of microorganisms to carry oligosaccharides provides several advantages over previously available methods for delivering oligosaccharide-based molecules to humans and other animals. For example, digestive enzymes that are present in certain host environments (e.g., the small intestine) can cleave free oligosaccharides, reducing their utility for treatment of infections and other conditions in more distal regions of the gut. The invention circumvents this problem by virtue of having the oligosaccharides carried by microorganisms. For gastrointestinal applications, for example, the microorganisms preferably are strains that are resistant to conditions found in the gut.

An illustrative example of the invention involves a recombinant delivery microorganism that displays a chimeric lipopolysaccharide structure, the terminal sugars of which constitute a Shiga toxin receptor mimic. These recombinant delivery microorganism are effective at protecting susceptible cells from attack by the Shiga toxin whose receptor they mimic. The use of a chimeric carbohydrate moiety such as lipopolysaccharide means that the endogenous transport machinery of the delivery microorganism is used to appropriately display the receptor mimic. The effectiveness of providing a receptor mimic on the surface of a recombinant microorganism has ramifications in relation to a broader range of toxins than simply Shiga toxins; it also has ramifications for other toxins such as those discussed above whose action requires recognition of oligosaccharide receptors. Additionally the receptors for adhesins of certain pathogenic microorganisms (including bacteria, viruses and parasites, for example) are structurally similar to receptors for certain toxins, and the provision of receptors for such adhesins on a microorganism surface should have a protective effect by interfering with the pathogen and/or its capacity to infect host cells. Moreover the chimeric carbohydrate still has a protective effect if secreted or released into the environment, not being attached to the delivery microorganism surface. This invention also opens the way to use non-chimeric carbohydrates as competitive inhibitors for toxins and pathogenic micro-organisms.

Recombinant Microorganisms

The invention provides recombinant microorganisms that synthesize specific oligosaccharide structures that have a desired biological activity, e.g., binding to a receptor, toxin, or other molecule. The microorganisms can also be used to carry the oligosaccharide structures to a target site (e.g., an animal membrane). There may be inherent advantages in having the receptor formed by microorganism in situ, including cost, capacity of the delivery microorganism to undergo multiplication in the gut, expression of a high density of receptor mimics on the cell surface, and display of the receptor mimic in an appropriate conformation.

Suitable microorganisms include, for example, bacteria, fungi, yeast, and other cells that include an acceptor moiety that can serve as a substrate for a glycosyltransferase or other enzyme involved in synthesis of the desired oligosaccharide. The microorganisms preferably display the oligosaccharide on a surface of the microorganism, or in another form that is exposed to the surrounding environment after administration.

The microorganisms include at least one heterologous or exogenous nucleic acid that encodes one of the glycosyltransferases or other enzymes that is involved in synthesizing the oligosaccharide structure. More than one exogenous nucleic acids can be present in a single microorganism.

The glycosyltransferases or other enzymes add or remove a sugar from an acceptor molecule. The acceptor molecule can be a glycolipid, glycoprotein, or other carbohydrate that is anchored in the delivery microorganism, for example, capsular polysaccharides of either gram-negative or gram-positive bacteria, or teichoic acids and lipoteichoic acids of gram-positive bacteria. In another form the acceptor molecule is one that is normally secreted into the external milieu, such as exopolysaccharides of either Gram-negative or Gram-positive bacteria.

1. Glycosyltransferases

The recombinant cells of the invention contain at least one heterologous gene that encodes a glycosyltransferase or other enzyme that is involved in oligosaccharide synthesis. Many glycosyltransferases are known, as are their polynucleotide sequences. See, e.g., "The WWW Guide To Cloned Glycosyltransferases," (www.vei.co.uk/TGN/gt guide.htm). Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the cells of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, and oligosaccharyltransferases. These glycosyltransferases include those obtained from both eukaryotes and prokaryotes. Many mammalian glycosyltransferases have been cloned and expressed and the recombinant proteins have been characterized in terms of donor and acceptor specificity and they have also been investigated through site directed mutagenesis in attempts to define residues involved in either donor or acceptor specificity (Aoki et al. (1990) *EMBO. J.* 9: 3171–3178; Harduin-Lepers et al. (1995) *Glycobiology* 5(8): 741–758; Natsuka and Lowe (1994) *Current Opinion in Structural Biology* 4: 683–691; Zu et al. (1995) *Biochem. Biophys. Res. Comm.* 206(1): 362–369; Seto et al. (1995) *Eur. J. Biochem.* 234: 323–328; Seto et al. (1997) J. Biol. Chem. 272: 14133–141388).

In some embodiments, the glycosyltransferase is a fucosyltransferase. A number of fucosyltransferases are known to those of skill in the art. Briefly, fucosyltransferases include any of those enzymes which transfer L-fucose from GDP-fucose to a hydroxy position of an acceptor sugar. In some embodiments, for example, the acceptor sugar is a GlcNAc in a βGal(1→4)βGlcNAc group in an oligosaccharide glycoside. Suitable fucosyltransferases for this reaction include the known Galβ(1→3,4)GlcNAc α(1→3,4) fucosyltransferase (FTIII E.C. No. 2.4.1.65) which is obtained from human milk (see, Palcic, et al., *Carbohydrate Res.* 190:1–11 (1989); Prieels, et al., J. Biol. Chem. 256:10456–10463 (1981); and Nunez, et al., *Can. J. Chem.* 59:2086–2095 (1981)) and the Galβ(1→4)GlcNAc α(1→3) fucosyltransferases (FTIV, FTV, FTVI, and FTVII, E.C. No. 2.4.1.65) which are found in human serum. A recombinant form of Galβ(1→3,4)GlcNAc α(1→3,4)fucosyltransferase is also available (see, Dumas, et al., *Bioorg. Med. Letters* 1:425–428 (1991) and Kukowska-Latallo, et al., *Genes and Development* 4:1288–1303 (1990)). Other exemplary fucosyltransferases include α1,2 fucosyltransferase (E.C. No. 2.4.1.69). Enzymatic fucosylation may be carried out by the methods described in Mollicone, et al., *Eur. J. Biochem.* 191:169–176 (1990) or U.S. Pat. No. 5,374,655.

In another group of embodiments, the glycosyltransferase is a galactosyltransferase. When a galactosyltransferase is used, the reaction medium will preferably contain, in addition to the cell that contains the exogenous galactosyltransferase gene, UDP-Gal and/or a mechanism for its synthesis, an oligosaccharide acceptor moiety, and a divalent metal cation. Exemplary galactosyltransferases include α(1,3) galactosyltransferases (E.C. No. 2.4.1.151, see, e.g., Dabkowski et al., *Transplant Proc.* 25:2921 (1993) and Yamamoto et al. *Nature* 345:229–233 (1990), bovine (GenBank j04989, Joziasse et al. (1989) *J. Biol. Chem.* 264:14290–14297), murine (GenBank m26925; Larsen et al. (1989) *Proc. Nat'l. Acad. Sci. USA* 86:8227–8231), porcine (GenBank L36152; Strahan et al (1995) *Immunogenetics* 41:101–105)). Another suitable α2,3 galactosyltransferase is that which is involved in synthesis of the blood group B antigen (EC 2.4.1.37, Yamamoto et al. (1990) *J. Biol. Chem.* 265:1146–1151 (human)). Also suitable for use in the methods and recombinant cells of the invention are α(1,4) galactosyltransferases, which include, for example, EC 2.4.1.90 (LacNAc synthetase) and EC 2.4.1.22 (lactose synthetase) (bovine (D'Agostaro et al (1989) Eur. J. Biochem. 183:211–217), human (Masri et al. (1988) *Biochem. Biophys. Res. Commun.* 157:657–663), murine Nakazawa et al. (1988) J. Biochem. 104:165–168), as well as E.C.

2.4.1.38 and the ceramide galactosyltransferase (EC 2.4.1.45, Stahl et al. (1994) *J. Neurosci. Res.* 38:234–242). Other suitable galactosyltransferases include, for example, a1, α1,2 galactosyltransferases (from e.g., *Schizosaccharomyces pombe*, Chapel et al (1994) *Mol. Biol. Cell* 5:519–528).

Sialyltransferases are another type of glycosyltransferase that is useful in the recombinant cells of the invention. Examples of sialyltransferases that are suitable for use in the present invention include ST3Gal III (preferably a rat ST3Gal III), ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al. (1996) *Glycobiology* 6: v–xiv). An exemplary α(2,3)sialyltransferase referred to as α(2,3) sialyltransferase (EC 2.4.99.6) transfers sialic acid to the non-reducing terminal Gal of a Galβ1→3Glc disaccharide or glycoside. See, Van den Eijnden et al., *J. Biol. Chem.*, 256:3159 (1981), Weinstein et al., *J. Biol. Chem.*, 257:13845 (1982) and Wen et al., *J. Biol. Chem.*, 267:21011 (1992). Another exemplary α2,3-sialyltransferase (EC 2.4.99.4) transfers sialic acid to the non-reducing terminal Gal of the disaccharide or glycoside. See, Rearick e al., *J. Biol. Chem.*, 254:4444 (1979) and Gillespie et al., *J. Biol. Chem.*, 267:21004 (1992). Further exemplary enzymes include Gal-β-1,4-GlcNAc α-2,6 sialyltransferase (See, Kurosawa et al. Eur. J. Biochem. 219: 375–381 (1994)).

Other glycosyltransferases that can be used the recombinant host cells of the invention have been described in detail. In particular, the glycosyltransferase can also be, for instance, glucosyltransferases, e.g., Alg8 (Stagljov et al., Proc. Natl. Acad. Sci. USA 91:5977 (1994)) or Alg5 (Heesen et al. *Eur. J. Biochem.* 224:71 (1994)), N-acetylgalactosaminyltransferases such as, for example, α(1,3) N-acetylgalactosaminyltransferase, β(1,4) N-acetylgalactosaminyltransferases (Nagata et al. *J. Biol. Chem.* 267:12082–12089 (1992) and Smith et al *J. Biol Chem.* 269:15162 (1994)) and polypeptide N-acetylgalactosaminyltransferase (Homa et al *J. Biol Chem.* 268:12609 (1993)). Suitable N-acetylglucosaminyltransferases include GnTI (2.4.1.101, Hull et al., BBRC 176:608 (1991)), GnTII, and GnTIII (Ihara et al. *J. Biochem.* 113:692 (1993)), GnTV (Shoreiban et al. *J. Biol. Chem.* 268: 15381 (1993)), O-linked N-acetylglucosaminyltransferase (Bierhuizen et al. *Proc. Natl. Acad. Sci. USA* 89:9326 (1992)), N-acetylglucosamine-1-phosphate transferase (Rajput et al. *Biochem J.*285:985 (1992), and hyaluronan synthase. Suitable mannosyltransferases include α(1,2) mannosyltransferase, α(1,3) mannosyltransferase, β(1,4) mannosyltransferase, Dol-P-Man synthase, OCh1, and Pmt1.

Prokaryotic glycosyltransferases are also useful in the recombinant cells. Such glycosyltransferases include enzymes involved in synthesis of lipooligosaccharides (LOS), which are produced by many gram negative bacteria. The LOS typically have terminal glycan sequences that mimic glycoconjugates found on the surface of human epithelial cells or in host secretions Preston et al. (1996) Critical Reviews in Microbiology 23(3): 139–180). Thus, the use of such enzymes is particularly useful for making a recombinant delivery microorganism that mimics these receptor glycoconjugates and thus blocks binding of the pathogenic LOS-containing organisms. Such enzymes include, but are not limited to, the proteins of the rfa operons of species such as *E. coli* and *Salmonella typhimurium*, which include a β1,6 galactosyltransferase and a β1,3 galactosyltransferase (see, e.g., EMBL Accession Nos. M80599 and M86935 (*E. coli*); EMBL Accession No. S56361 (*S. typhimurium*)), a glucosyltransferase (Swiss-Prot Accession No. P25740 (*E. coli*), an β1,2-glucosyltransferase (rfaJ) (Swiss-Prot Accession No. P27129 (*E. coli*) and Swiss-Prot Accession No. P19817 (*S. typhimurium*)), and an β1,2-N-acetylglucosaminyltransferase (rfaK)(EMBL Accession No. U00039 (*E. coli*). Other glycosyltransferases for which amino acid sequences are known include those that are encoded by operons such as rfaB, which have been characterized in organisms such as *Klebsiella pneumoniae, E. coli, Salmonella typhimurium, Salmonella enterica, Yersinia enterocolitica, Mycobacterium leprosum*, and the rhl operon of *Pseudomonas aeruginosa*.

Also suitable for use in the cells of the invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the $P^k$ blood group trisaccharide sequence, D-galactosyl-α-1,4-D-galactosyl-β-1,4-D-glucose, which have been identified in the LOS of the mucosal pathogens *Neisseria gonnorhoeae* and *N. meningitidis* (Scholten et al. (1994) *J. Med. Microbiol.* 41: 236–243). The genes from *N. meningitidis* and *N. gonorrhoeae* that encode the glycosyltransferases involved in the biosynthesis of these structures have been identified from *N. meningitidis* immunotypes L3 and L1 (Jennings et al. (1995) *Mol. Microbiol.* 18: 729–740) and the *N. gonorrhoeae* mutant F62 (Gotshlich (1994) *J. Exp. Med.* 180: 2181–2190). In *N. meningitidis*, a locus consisting of three genes, lgtA, lgtB and lg E, encodes the glycosyltransferase enzymes required for addition of the last three of the sugars in the lacto-N-neotetraose chain (Wakarchuk et al. (1996) *J. Biol. Chem.* 271: 19166–73). Recently the enzymatic activity of the lgtB and lgtA gene product was demonstrated, providing the first direct evidence for their proposed glycosyltransferase function (Wakarchuk et al. (1996) *J. Biol. Chem.* 271 (45): 28271–276). In *N. gonorrhoeae*, there are two additional genes, lgtD which adds β-D-GalNAc to the 3 position of the terminal galactose of the lacto-N-neotetraose structure and lgtC which adds a terminal α-D-Gal to the lactose element of a truncated LOS, thus creating the $P^k$ blood group antigen structure (Gotshlich (1994), supra.). In *N. meningitidis*, a separate immunotype L1 also expresses the $P^k$ blood group antigen and has been shown to carry an lgtC gene (Jennings et al. (1995), supra.). Neisseria glycosyltransferases and associated genes are also described in U.S. Pat. No. 5,545, 553 (Gotschlich). An α1,3-fucosyltransferase gene from *Helicobacter pylori* has also been characterized (Martin et al. (1997) *J. Biol. Chem.* 272: 21349–21356).

In some embodiments, the recombinant delivery cells of the invention can contain at least one heterologous gene that encodes a sulfotransferase. Such cells also produce the active sulfating agent 3'-phosphoadenosine-5'-phosphosulfate (PAPS). Incorporation of one or more sulfotransferase genes into a cell that also produces PAPS, either naturally or through the addition of the PAPS cycle regeneration enzymes, provides one with cells that can sulfate oligosaccharides or polysaccharides. Suitable sulfotransferase include, for example, chondroitin-6-sulphotransferase (chicken cDNA described by Fukuta et al. (1995) *J. Biol. Chem.* 270:18575–18580; GenBank Accession No. D49915), glycosaminoglycan N-acetylglucosamine N-deacetylase/N-sulphotransferase 1 (Dixon et al. (1995) *Genomics* 26:239–241; UL18918), and glycosaminoglycan N-acetylglucosamine N-deacetylase/N-sulphotransferase 2 (murine cDNA described in Orellana et al. (1994) *J. Biol. Chem.* 269:2270–2276 and Eriksson et al. (1994) *J. Biol. Chem.* 269:10438–10443, human cDNA described in GenBank Accession No. U2304).

Glycosyltransferase nucleic acids, and methods of obtaining such nucleic acids, are known to those of skill in the art. Glycosyltransferase nucleic acids (e.g, cDNA, genomic, or subsequences (probes)) can be cloned, or amplified by in vitro methods such as the polymerase chain reaction (PCR), the ligase chain reaction (LCR), the transcription-based amplification system (TAS), the self-substained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current Protocols in Molecular Biology,* F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017, 478; and Carr, European Patent No. 0,246,864. Examples of techniques sufficient to direct persons of skill through in vitro amplification methods are found in Berger, Sambrook, and Ausubel, as well as Mullis et al. (1987) U.S. Pat. No. 4,683,202; *PCR Protocols A Guide to Methods and Applications* (Innis et al., eds) Academic Press Inc. San Diego, Calif. (1990) (Innis); Arnhein & Levinson (Oct. 1, 1990) *C&EN* 36–47; *The Journal Of NIH Research* (1991) 3: 81–94; (Kwoh et al. (1989) *Proc. Nat'l. Acad. Sci. USA* 86: 1173; Guatelli et al. (1990) *Proc. Nat'l. Acad. Sci. USA* 87, 1874; Lomell et al. (1989) *J. Clin. Chem.,* 35: 1826; Landegren et al., (1988) *Science* 241: 1077–1080; Van Brunt (1990) *Biotechnology* 8: 291–294; Wu and Wallace (1989) *Gene* 4: 560; and Barringer et al. (1990) *Gene* 89: 117.

DNA that encodes glycosyltransferase proteins or subsequences, as well as DNA that encodes the enzymes involved in formation of nucleotide sugars described below, can be prepared by any suitable method as described above, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.,* 22: 1859–1862; and the solid support method of U.S. Pat. No. 4,458,066. In one preferred embodiment, a nucleic acid encoding a glycosyltransferase can be isolated by routine cloning methods. A nucleotide sequence of a glycosyltransferase as provided in, for example, GenBank or other sequence database can be used to provide probes that specifically hybridize to a glycosyltransferase gene in a genomic DNA sample, or to a glycosyltransferase mRNA in a total RNA sample (e.g., in a Southern or Northern blot). Once the target glycosyltransferase nucleic acid is identified, it can be isolated according to standard methods known to those of skill in the art (see, e.g., Sambrook et al. (1989) *Molecular Cloning: A Laboratory Manual,* 2nd Ed., Vols. 1–3, Cold Spring Harbor Laboratory; Berger and Kimmel (1 987) *Methods in Enzymology,* Vol. 152: *Guide to Molecular Cloning Techniques,* San Diego: Academic Press, Inc.; or Ausubel et al. (1987) *Current Protocols in Molecular Biology,* Greene Publishing and Wiley-Interscience, New York).

A glycosyltransferase nucleic acid can also be cloned by detecting its expressed product by means of assays based on the physical, chemical, or immunological properties. For example, one can identify a cloned glycosyltransferase nucleic acid by the ability of a polypeptide encoded by the nucleic acid to catalyze the transfer of a monosaccharide from a donor to an acceptor moiety. In a preferred method, capillary electrophoresis is employed to detect the reaction products. This highly sensitive assay involves using either monosaccharide or disaccharide aminophenyl derivatives which are labeled with fluorescein as described in Wakarchuk et al. (1996) *J. Biol. Chem.* 271 (45): 28271–276. For example, to assay for a Neisseria lgtC enzyme, either FCHASE-AP-Lac or FCHASE-AP-Gal can be used, whereas for the Neisseria lgtB enzyme an appropriate reagent is FCHASE-AP-GlcNAc (Id.).

As an alternative to cloning a glycosyltransferase gene, a glycosyltransferase nucleic acid can be chemically synthesized from a known sequence that encodes a glycosyltransferase. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is often limited to sequences of about 100 bases, longer sequences may be obtained by the ligation of shorter sequences.

Alternatively, subsequences can be cloned and the appropriate subsequences cleaved using appropriate restriction enzymes. The fragments may then be ligated to produce the desired DNA sequence.

The glycosyltransferase-encoding nucleic acids can be cloned using DNA amplification methods such as polymerase chain reaction (PCR). Thus, for example, the nucleic acid sequence or subsequence is PCR amplified, using a sense primer containing one restriction site (e.g., NdeI) and an antisense primer containing another restriction site (e.g., HindIII). This will produce a nucleic acid encoding the desired glycosyltransferase sequence or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the sequence information provided in GenBank or other sources. Appropriate restriction sites can also be added to the nucleic acid encoding the glycosyltransferase protein or protein subsequence by site-directed mutagenesis. The plasmid containing the glycosyltransferase-encoding nucleotide sequence or subsequence is cleaved with the appropriate restriction endonuclease and then ligated into an appropriate vector for amplification and/or expression according to standard methods.

Other physical properties of a polypeptide expressed from a particular nucleic acid can be compared to properties of known glycosyltransferases to provide another method of identifying glycosyltransferase-encoding nucleic acids. Alternatively, a putative glycosyltransferase gene can be mutated, and its role as a glycosyltransferase established by detecting a variation in the structure of an oligosaccharide normally produced by the glycosyltransferase.

In addition to, or instead of, glycosyltransferases, one can use a different enzyme that adds sugar residues to, or removes from, an acceptor molecule. Accordingly, the invention provides recombinant microorganisms that have an exogenous nucleic acid that encodes an enzyme such as a sialidase (e.g., trans-sialidase), mannosidase, galactosidase, glucosidase. Through use of such enzymes, an acceptor molecule can be modified to obtain an oligosaccharide structure that exhibits the desired biological property.

In some embodiments, it may be desirable to modify the glycosyltransferase or accessory enzyme nucleic acids. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) Gene 8:81–97, Roberts et al. (1987) Nature 328: 731–734. For example, one can modify the glycosyltransferase gene to change the specificity or, for example, to stabilise a gene that might be subject to phase variation during normal cellular processes such as replication.

In a preferred embodiment, the recombinant nucleic acids present in the cells of the invention are modified to include preferred codons which enhance translation of the nucleic acid in a selected organism (e.g., yeast preferred codons are substituted into a coding nucleic acid for expression in yeast).

2. Accessory enzymes involved in nucleotide sugar formation

In selecting the delivery microorganism it may be found that a suitable complement of endogenous glycosyltransferases are already present but there is a surfeit of enzymes for the production of precursor nucleotide sugars, such enzyme could include epimerases, dehydrogenases, transmutases. The addition of one of these enzyme can be sufficient to provide for a chimeric carbohydrate that is capable of acting as a receptor mimic, more commonly it is anticipated that a gene encoding an exogenous enzyme required for nucleotide precursor production may need to be introduced in addition to the one or more exogenous glycosyl transferases.

Accordingly, the recombinant microorganisms of the invention can also include, in addition to or in place of the nucleic acid encoding a glycosyltransferase or other enzyme involved in oligosaccharide synthesis, at least one heterologous nucleic acid that encodes an accessory enzyme. Accessory enzymes include, for example, those enzymes that are involved in the formation of a nucleotide sugar. The accessory enzyme can be involved in attaching the sugar to a nucleotide, or can be involved in making the sugar or the nucleotide, for example. Examples of nucleotide sugars that are used as sugar donors by glycosyltransferases include, for example, GDP-Man, UDP-Glc, UDP-Gal, UDP-GlcNAc, UDP-GalNAc, CMP-sialic acid, UDP-xylose, GDP-Fuc, GDP-GlcNAc, among others.

Accessory enzymes that are involved in synthesis of nucleotide sugars are well known to those of skill in the art. For a review of bacterial polysaccharide synthesis and gene nomenclature, see, e.g., Reeves et al., Trends Microbiol. 4: 495–503 (1996). The methods described above for obtaining glycosyltransferase-encoding nucleic acids are also applicable to obtaining nucleic acids that encode enzymes involved in the formation of nucleotide sugars. For example, one can use one of nucleic acids known in the art directly or as a probe to isolate a corresponding nucleic acid from other organisms of interest.

3. Expression cassettes and host cells for expressing the fusion polypeptides

A wide variety of microorganisms are useful for synthesis and/or carrying of oligosaccharides according to the methods of the invention. To obtain expression of the glycosyltransferase and/or other enzymes that are involved in synthesis of the binding moieties, the nucleic acids that encode the enzymes are placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes."

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., Nature (1 977) 198: 1056), the tryptophan (trp) promoter system (Goeddel et al., Nucleic Acids Res. (1980) 8: 4057), the tac promoter (DeBoer, et al., Proc. Natl. Acad. Sci. U.S.A. (1 983) 80:21–25); and the lambda-derived $P_L$ promoter and N-gene ribosome binding site (Shimatake et al., Nature (1981) 292: 128). The particular promoter system is not critical to the invention, any available promoter that functions in prokaryotes can be used.

For expression of fusion polypeptides in prokaryotic cells other than E. coli, a promoter that functions in the particular prokaryotic species is required. Such promoters can be obtained from genes that have been cloned from the species, or heterologous promoters can be used. For example, a hybrid trp-lac promoter that functions in Bacillus in addition to E. coil is described in WO9820111.

A ribosome binding site (RBS) is conveniently included in the expression cassettes of the invention. An RBS in E. coli, for example, consists of a nucleotide sequence 3–9 nucleotides in length located 3–11 nucleotides upstream of the initiation codon (Shine and Dalgarno, Nature (1975)254: 34; Steitz, In Biological regulation and development: Gene expression (ed. R. F. Goldberger), vol. 1, p. 349, 1979, Plenum Publishing, NY).

For expression of the fusion polypeptides in yeast, convenient promoters include GAL1-10 (Johnson and Davies (1984) *Mol. Cell. Biol.* 4:1440–1448) ADH2 (Russell et al. (1983) *J. Biol. Chem.* 258:2674–2682), PHO5 (*EMBO J.* (1982) 6:675–680), and MFa (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181–209). Another suitable promoter for use in yeast is the ADH2/GAPDH hybrid promoter as described in Cousens et al., *Gene* 61:265–275 (1987). For filamentous fungi such as, for example, strains of the fungi Aspergillus (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

Either constitutive or regulated promoters can be used in the microorganisms of the invention. Regulated promoters can be advantageous because the host cells can be grown to high densities before expression of the glycosyltransferases is induced. High level expression of heterologous proteins slows cell growth in some situations. An inducible promoter is a promoter that directs expression of a gene where the level of expression is alterable by environmental or developmental factors such as, for example, temperature, pH anaerobic or aerobic conditions, light, transcription factors and chemicals. Such promoters are referred to herein as "inducible" promoters, which allow one to control the timing of expression of the glycosyltransferase or other enzyme involved in nucleotide sugar synthesis. Such promoters can also be useful for suppressing synthesis of the oligosaccharide until after the organisms have been administered. At a desired time a stimulus can be applied, so that the oligosaccharide structure is synthesized after the delivery microorganism has arrived at a desired target site.

For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.;* Tabor et al. (1985) *Proc. Nat'l. Acad. Sci. USA* 82: 1074–1078). These promoters and their use are discussed in Sambrook et al., supra. A particularly preferred inducible promoter for expression in prokaryotes is a dual promoter that includes a lac promoter component linked to a promoter component obtained from a gene or genes that encode enzymes involved in galactose metabolism (e.g., a promoter from a UDPgalactose 4-epimerase gene (galE)). The dual lac-gal promoter, which is described in PCT Patent Application Publ. No. WO98/20111, provides a level of expression that is greater than that provided by either promoter alone.

DNA encoding the exogenous genes can be carried on a non-integrated vector such as a plasmid, selected to be stable within the delivery microorganism. Such vectors are known to those skilled in the art. One benefit in having the DNA in a non-integrated form is that a high copy number of the encoding DNA can mean that where competitive addition of sugars to an intermediate acceptor molecule is required, the enzyme encoded by the high copy number gene can prevail. An alternative is to have the exogenous gene or genes incorporated into the microorganism chromosome. This tends to provide a greater measure of stability.

Methods for cloning a glycosyltransferase gene from one species to another to make chimeric lipopolysacchacrides are described in, for example, Phillips et al, (2000) *J. Biol. Chem.* 275:4747–4758 and Abu Kwaik et al., (1991) *Molec. Microbiol.* 5:2475–2480.

Methods of Administering Recombinant Microorganisms

The invention also provides methods of administering the recombinant microorganisms, or oligosaccharide-containing fractions thereof, to a human or other animal. The microorganisms or fractions thereof can thus function as carriers for the oligosaccharides. The oligosaccharides are preferably displayed on the surface of the microorganism, or are otherwise exposed to the environment after administration to the animal. Such exposure can result from the natural expression, or from processing of the microorganism after synthesis of the oligosaccharide. For example, a membrane preparation, lipopolysaccharide, glycoprotein, glycolipid, or other moiety that upon which an oligosaccharide can be attached can be administered. The preparation can be used unpurified, or partially or completely purified. It is often desirable that the preparation is at least substantially free of nucleic acids from the microorganism.

The oligosaccharide-containing binding moieties can be delivered to, for example, a mucosal surface of a mammal. Such mucosal surfaces include, for example, the gastrointestinal tract, the pulmonary and bronchial tissues, vaginal surfaces. The binding moieties can also be administered to, for example, the eye, skin, etc.

The quantity administered is chosen to be sufficient is have the desired effect. For example, in some applications the amount of binding moiety administered is sufficient to reduce adherence of a pathogen or a toxin produced by a pathogen to a mucosal or other surface.

The delivery microorganism is chosen to be non-harmful when administered. It is also possible that a pathogen or an organism with potentially adverse health effects is used, and this would be administered in an attenuated form, or may be administered in a killed form. The killing of the microorganism is to be conducted under standard conditions that maintain the chimeric carbohydrate molecule, and in particular the receptor mimic intact. Examples of methods of providing killed microorganism include, but are not limited to, treatment with chemical agents such as formalin, thiomersal, or streptomycin or other bactericidal antibiotic, or exposure to heat or UV iradiation. Bacterial ghosts generated by induction of a bacteriophage lysis protein may also be a suitable delivery vehicle for receptor mimics, as would liposomes incorporating the chimeric LPS. In the alternative purified membrane vesicles (MVs) can be used. MVs are naturally released by gram negative bacteria and can be described as blebs of the outer membrane. Purified lipopolysaccharide can be used however preferably the delivery microorganism expresses mutations which decrease endotoxin activity of LPS, and such mutations can include phoP$^c$(67) or msbB (waaN) (68, 69).

The delivery microorganism can be utilised in a live form so that it can multiply in vivo at least to a limited extent, thereby producing more receptor mimics, so that smaller doses can be effective. However, particularly for administration to humans, it is preferable that an at least partially purified preparation of the oligosaccharides is used.

The stomach of an individual presents a considerable barrier to the introduction of microorganism and acid labile macromolecules. It can be desirable to provide for some acid resistance. For example a particle can be delivered that has a protective coating, such as those that are commonly used in the delivery of pharmaceuticals, which can then be selectively released either in the small intestine, large intestine or both. Such coatings and capsules are well known. An alternative approach can be to make the delivery microorganism more acid tolerant, for example the delivery microorganism could have a constitutive acid-tolerance response. It is sometimes desired to grow the delivery microorganism in media that enhance their capacity to pass the acid barrier of the stomach; for example the culture can be grown under low pH conditions to induce acid tolerance.

Additionally one can provide for some resistance to anti microbial activity that is presented by the resident microflora. Thus for example the delivery microorganism could be modified or chosen to be resistant to the major families of colicins (for example Col E1, E2 and E3) by the introduction of, for example, the btuB mutation.

The choice of delivery microorganism is wide insofar as what is required is that the organism is capable of expressing the chimeric carbohydrate molecule being delivered to the gut. The delivery mode can be in a protected environment such as by being coated or inside a capsule, and thus the organism need not necessarily be acid resistant. It is also possible that the delivery microorganism need not survive in the gut and these measures may also be useful for delivery of kllled microorganism or partially or fully purified carbohydrates carrying the receptor mimic. All that is required is that the receptor mimic be exposed in sufficient quantities to adsorb toxin or the pathogenic organism. It is preferred however that the organism does survive and grow and therefore presents an increasing level of the chimeric carbohydrate for adsorption, accordingly it is desired that the organism is resistant to conditions found in the gut and thus is an enteric organism.

The delivery microorganism can be selected from the genuses Escherichia and Salmonella, and more preferably *Escherichia coli* and *Salmonella enterica* sv typhimurium. However, certain other bacterial genera may be convenient to use, notably those such as Acidophilus, Lactobacillus, Lactococcus or Bifidobacterium, which being food bacteria, are known to be safe to administer orally to humans, and are also capable of survival in the gut. These later organisms have, in common with Escherichia and Salmonella, been relatively well characterised.

To be more effective it is desired that the delivery microorganism properly exposes the receptor mimic in as effective a manner as possible. Accordingly it is desired that the delivery microorganism does not produce or has a limited capacity to produce any of the following: O-antigen, a slime layer, capsule or exopolysaccharide, where such carbohydrates are not the carrier of the receptor mimic. These molecules might otherwise mask the receptor mimic.

It is also desirable that the microorganism expressing the receptor mimic colonizes the gastrointestinal tract for only a limited period of time, so as not to perturb normal receptor-ligand interactions, or disturb the state of immune tolerance which prevents elicitation of potentially deleterious anti-receptor antibodies. Incorporation of an inducible suicide gene may help eliminate the recombinant microorganism from the host when its presence is no longer necessary. An example of such as system is the stochastic lethal containment system described by Klemm et al. (42).

The recombinant microorganisms of the invention find use human (in pharmaceutical use, and also for veterinary use. For example, microorganisms that display an appropriate oligosaccharide for animal pathogens are useful to treat livestock and other animals of interest. Such animals include, but are not limited to, humans, pigs, cows, horses, canines, felines, chickens, turkeys, goats, rabbits, sheep, geese, ducks.

In a second form of the second aspect the invention provides a recombinant microorganism expressing one or more exogenous sugar transferases and an acceptor molecule, said one or more exogenous sugar transferases being specific for the transfer of one or more sugar residues represented progressively from a non reducing terminal end of a receptor of either a toxin or an adhesin of a pathogenic organism, said delivery microorganism expressing the exogenous sugar transferases, and progressively transferring said one or more sugar resides onto the acceptor molecule to thereby form a chimeric carbohydrate molecule with an exposed receptor mimic, said exposed receptor mimic capable of binding the toxin or the adhesin.

Suitable excipients for the delivery of the receptor mimic are readily ascertainable, and examples can be found in Remington's Pharmaceutical Sciences, Mack Publishing Company, 16th Edition, 1980. Similarly methods for delivery by packing in capsules or within a matrix such as a tablet can be found in the same reference.

Uses of the Recombinant Microorganisms

The recombinant microorganisms of the invention are useful for a wide variety of applications upon administration to a human or other mammal.

1. Toxins and Adhesins

The invention provides methods of reducing the amount of a toxin or a pathogenic organism from an environment. These methods involve introducing at least an inoculum of a recombinant microorganism into the environment. The recombinant microorganism carries a binding moiety that mimics a receptor of either the toxin or an adhesin of the pathogenic organism is exposed to the environment for contact with the toxin or adhesin. The oligosaccharide-containing binding moiety can be, for example, anchored to the outer surface of the microorganism, or secreted into the environment.

For example, a recombinant microorganism that displays a chimeric carbohydrate molecule that functions as a mimic of a receptor for a toxin, or for an adhesin of a pathogenic organism, can be administered to block binding of the toxin and/or pathogenic organism to the receptor. The chimeric receptor can be chosen to bind toxins, adhesins of enteric bacterial or viral or parasitic pathogens, or lectins associated with these organisms.

The toxins include those made in the gut and can be selected from, but not limited to, a group comprising shiga toxins, clostridial toxins, cholera toxins, *E. coli* enterotoxins, and Staphylococcal enterotoxins.

As an illustrative example, the shiga toxins can be selected from the group comprising, Stx, Stx1, Stx2, Stx2c, Stx2d, and Stx2e. In the case where the shiga toxin is Stx, Stx1, Stx2, Stx2c, or Stx2d, the receptor mimic preferably is formed by a terminal sugar moiety of Galα[1→4]Galβ[1→4]Glc. The one or more transferases is either an α1→4 galactosyl transferase capable of forming an α1→4 bond with a galactose residue bonded by a β1→4 bond to a glucose on the acceptor molecule, or both an α1→4 galactosyl transferase and α1→4 galactosyl transferase capable of forming a β1→4 bond to a glucose on the acceptor molecule. While it might be desirable that the exogenous glycosyl transferases add sugars to a sugar residue of the acceptor molecule, it may be adequate that the glycosyl transferases compete with an endogenous transferase, and that the acceptor molecule is a partially completed endogenous oligosaccharide or polysaccharide.

Where the shiga toxin is Stx2e the an alternative oligosaccharide moiety of the receptor for a terminal chain is suggested to be GalNAcβ[1→3]Galα[1→4]Galβ[1→4]Glc. The one or more transferases are selected to transfer one or more sugars selected from the terminal portion of the receptor for Stx2e. In addition to those transferases listed above, the one or more transferases are selected to include a β1→3GalNAc transferase capable of forming a β1→3 bond with a galactose residue.

strains of *Haemophilus influenzae* as one of their variable LOS components, and genetic material from these strains can be used to construct a recombinant receptor mimic.

The clostridial toxins include, for example, tetanus toxin, botulinum toxin, *C. difficile* toxins A and B. The natural receptor for *C. difficile* toxin A is known to contain a Galβ[1→4]GlcNAc moiety. Also, however, Galα[1→3]Galβ[1→4]GlcNAc- or Galα[1→3]Galβ[1→4]Glc- are also known to interact with toxin A. The receptor for botulinum toxin is also believed to be a sialic acid containing glycoprotein or glycolipid present on neurons.

The cholera toxins include cholera toxin and *E. coli* heat labile enterotoxin types I and II. The receptor for cholera toxin and *E. coli* heat labile enterotoxin type I is the ganglioside $G_{M1}$, the structure being as follows:

$$\text{Galβ[1} \longrightarrow \text{3]GalNAcβ[1} \longrightarrow \text{4]Galβ[1} \longrightarrow \text{4]Glc-ceramide}$$
$$|$$
$$\text{NeuNAcα[2} \longrightarrow \text{3]}$$

The receptor mimic can be chosen from 2 or more adjacent sugar residues in the configuration as set out immediately above.

The receptor mimic can be selected from any one of the receptors set out in Table 1.

TABLE 1

| Glycosyl structures of receptors for toxins and adhesins | |
|---|---|
| Galα[1→4]Galβ[1→4]Glc | Shiga toxin Stx1, Stx2, Stx2c, Stx2d, Stx2e, uropathogenic *E. coli* pap pili |
| Galα[1→4]Galβ | uropathogenic *E. coli* pap pili |
| GalNAcβ[1→3]Galα[1→4]Galβ[1→4]Glc | Shiga toxin Stx2e |
| Galβ[1→4]GlcNAc | *C. difficile* toxin A |
| Galα[1→3]Galβ[1→4]Glc | *C. difficile* toxin A |
| Galα[1→3]Galβ[1→4]GlcNAc | *C. difficile* toxin A |
| Galβ[1→4]GlcNAcβ[1→3]Galβ[1→4]Glc | *C. difficile* toxin A |
| Glcα[1→6]Glc— | *C. difficile* toxin B |
| Glcα[1→6]Glcα[1→6]Glc— | *C. difficile* toxin B |
| NeuNAc— | *C. botulinum* toxin |
| Galβ[1→3]GalNAcβ[1→4]Galβ[1→4]Glc—<br>\|<br>NeuNAcα[2→3] | *Vibrio cholera* toxin (CT), *E. coli* heat labile enterotoxin Type 1 |
| Galβ[1→3]GalNAcβ[1→4]Galβ[1→4]Glc— | Enterotoxigenic *E. coli* CFA adhesin, porcine enterotoxigenic *E. coli* K88ad fimbriae adhesin |
| GalNAcβ[1→4]Gal | Enterotoxigenic *E. coli* CS3 pili adhesin |
| GalNAc— | *Entamoeba histolyticum* trophozoite adherence |
| Gal— | *E. histolyticum* adherence |
| NeuGc→GM$_3$ | Porcine rotavirus adherence |
| NeuNAc→GM$_3$ | Porcine rotavirus adherence |

For Stx, Stx1, Stx2, Stx2c, and Stx2d receptors, the N-terminal sugar transferase gene can be selected from the group comprising lgtC of *N. meningitidis* or *N. gonorrhoeae* and the penultimate terminal sugar transferase gene may be selected from the group comprising lgtE of *N meningitidis* or *N. gonorrhoeae; Haemophilus influenzae* strain Rd is also known to contain genes encoding enzymes with analogous functions.

In the case of K88ad adhesin its receptor includes the lactoneotetraose series of glycolipids. These carbohydrates are produced by *N. Meningitidis, N. gonorrhoeae,* and some The receptor mimic can be a mimic of the natural receptor for adhesins or toxins produced by micro-organism selected from a group of genera comprising the following:—Escherichia, Salmonella, Shigella, Citrobacter, Helicobacter, Yersinia, Vibrio, Aeromonas, Campylobacter, Pseudomonas, Pasteurella, Neisseria, Haemophilus; Moraxella, Klebsiella, Staphylococcus, Streptococcus, Clostridium, Bacteriodes as well as viruses including rotavirus.

Additional examples of oligosaccharides that can be displayed on the microorganism, and examples of their use, are listed in Table 2.

TABLE 2

| Terminal Sugar | Example Oligosaccharide | Inhibits adhesion of: | Reference |
|---|---|---|---|
| Sialic acid | Ganglioside | *Staphylococcus pneumonia, H. influenzae, H. parainfluenza,* Pseudomonas | van Alphen et al. (1991) Infect. Immun. 59: 4473 |
| Sialic acid | LSTd, LSTc | *Staphylococcus pneumonia, H. influenzae, H. parainfluenza,* Pseudomonas | Simon et al., WO 96/40169 Simon et al., U.S. Pat. No. 5,736,533 Idanbaan-Heikkila et al. (1997) J. Infect. Dis. 176: 704–712 |
| Galactose | LNnT | *Staphylococcus pneumonia, H. influenzae, H. parainfluenza,* Pseudomonas | Simon et al., WO 96/40169 Simon et al., U.S. Pat. No. 5,736,533 Idanbaan-Heikkila et al. (1997) J. Infect. Dis. 176: 704–712 |
| Galactose | asialo-N-linked oligosaccharides | *Chlamydia trachomatis* | Kuo et al. (1996) J. Clin. Invest. 98: 2813–2818 |
| Mannose | Oligomannose | Acanthamoeba (e.g., adhesion to cells in eye) | Cao et al. (1998) J. Biol. Chem. 273: 15838 |
| Fucose | 2'Fucosides linked to Gal | *Candida ablicans* | Cameron, B J (1996) Infect. Immun. 64: 891 |
| Fucose | 2' and 3' fucosides (e.g., Lewis$^y$, Lewis$^b$ | *Helicobacter pylori* (e.g., adhesion to gastric cells) | Falk et al. (1993) Proc. Nat'l. Acad. Sci. USA 90: 2035 |
| GalNAc | Many | pulmonary pathogenic bacteria (see list in reference) | Krivan et al. (1988) Proc. Nat'l. Acad. Sci. USA 85: 6157 |
| Fucose or GlcNAc | Blood groups A, B, H | *Candida ablicans* | Critchley et al. (1987) J. Gen. Microbiol. 133: 637; Matei et al. (1997) Rev. Roum. Biochim. 34: 123 |
| GalNAc | Many | *Streptococcus pneumoniae* (e.g., adhesion to pulmonary cells) | Tuomanen et al. (WO 95/33467) |
| Sialic acid | | Enterotoxigenic *E. coli* | Sjoberg et al. (1988) Biochem. J. 255: 105 Schwertmann et al. (1999) J. Pediatric Gastroenterology and Nutrition 28: 257 |
| Sialic acid | | *Mycoplasma pneumonia* (e.g., ear infections, pneumonia) | Roberts et al. (1989) J. Biol. Chem. 264: 9289 Krivan et al., U.S. Pat. No. 5,089,479 |
| GalNAc—Gal \| Fuc | | *E. coli* heat-labile enterotoxin | Barra et al. (1992) Mol. Cell. Biochem. 115: 63–70 |
| Gal—Gal \| Fuc | | *E. coli* heat-labile enterotoxin | Barra et al. (1992) Mol. Cell. Biochem. 115: 63–70 |
| Sialic acid | 3' and 6' sialylosides (e.g., sialyllactose) | Adhesion to stomach | Zopf et al., U.S. Pat. No. 5,514,660 |
| Sialic acid | SLe$^x$ and SLe$^a$ | Inhibition of selectin-mediated inflammation | Paulson et al., U.S. Pat. No. 5,753,631 Ratcliffe et al., U.S. Pat. No. 5,576,305 DeFrees et al., U.S. Pat. No. 5,811,404 |
| Sialic acid | | *Streptococcus sanguis* (e.g., adhesion to human buccal epithelial cells) | Nesser et al. (1995) Glycobiology 5: 97 |

TABLE 2-continued

| Terminal Sugar | Example Oligosaccharide | Inhibits adhesion of: | Reference |
|---|---|---|---|
| Gal | LNnT, LNT, etc. | *Streptococcus pyogenes* (e.g., adhesion to pharyngeal cells) | Gaffar et al., U.S. Pat. No. 5,401,723 |
| Sialic acid | (incl. N-Ac-sialic acid; N-Gc-sialic acid, and 9-Oac-sialic acid | Influenza (e.g., adhesion to cells) | Eisen et al. (1997) Virology 232: 19 Gambaryan et al. (1997) Virology 232: 345 Connor et al. (1994) Virology 205: 17 Herrler et al. (1987) Virology 159: 102 |
| Fucose | 2'-fucosides such as 2'-fucosyllactose | *E. coli* and *Vibrio cholerae* (e.g., adhesion to gastrointestinal cells) | Prieto et al., WO 99/56754 |
| Fucose | 2'-fucosides | *Campylobacter jejuni* (e.g., adhesion to gastrointestinal cells) Stable enterotoxin (ST) of *E. coli* (binding of toxin to cells) | Newburg, D S (1997) Am. Symp. Nutritional Sci. 980S–984S |
| Sialic acid | | Paramyxovirus | Klenk et al. (1997) Nova Acta Leopoldina NF75, NR. 301, 131 |
| 9-OAc-sialic acid | | Human coronavirus Bovine coronavirus | Klenk et al. (1997) Nova Acta Leopoldina NF75, NR. 301, 131 |
| GalNAc | GalNAc(β1,3)Gal(α1,4)Gal | Parvovirus | Brown et al. (1993) Science 262: 114–117 |
| Sialic acid | 3' or 6'-sialosides | Cells and molecules involved in inflammation, irritation (e.g., of skin, intestine, etc) | U.S. patent application Ser. No. 09/123,251 (pending) |

In one form the acceptor molecule is a molecule which comprises at least some sugar units, these sugar units are normally exposed to the outside of the delivery microorganism. A preferred acceptor molecule is a lipopolysaccharide (LPS) molecule, and in which case the acceptor molecule is all or a portion of the core of the lipopolysaccharide.

In the case where the two terminal sugars of the chimeric receptor binds to Stx, Stx1, Stx2, Stx2c, and Stx2d, it may be preferred that the acceptor molecule has a terminal glucose. The acceptor molecules can be the LPS core of waaO mutants of *Escherichia coil* R1 wherein a terminal glucose is presented in the completed acceptor molecule of the mutant concerned. Alternatively a terminal glucose need not be provided, and the choice of bacterium based on LPS core structure is wide indeed. Specific examples of core structure that are suitable as acceptor molecules include but are not limited to the following, *Escherichia coli* R1, including waaO mutants thereof, *Escherichia coli* K-12 and various waa mutants thereof *Salmonella typhimurium* LT2, and various waa mutants thereof. It will be understood however that the range of molecules from which the acceptor molecule can be chosen is wide.

The elucidation of the nature of the oligosaccharide receptors is an ongoing endeavour, and more receptors for toxins and adhesins are being defined as time goes on. Selecting appropriate carbohydrate structures can be achieved by searching through a database of known carbohydrate structures, such as Carbbank, which is available over the internet; CDrom versions are also available from NBRF, National Biomedical Research Foundation, 3900 Reservoir Road, NW, Washington D.C. 20007 USA. Selecting appropriate nucleic acid sequences for expression of the desired glycosyl transferases can be achieved by searching through a database of genes encoding glycosyl transferases available over the internet, such as CAZy. This database is administered by AFMB-CNRS a contact being at 31 Chemin Joseph Aiguier F-13402 Marseille Cedex 20 (France). An alternative is to search for structures in the Chemical Abstracts. The search concerned will identify the sugar specificity of the transferase, the sugar to which it binds, the nature of the bond, and the overall nature of the acceptor molecule. Thus where the acceptor molecule is a LPS then a transferase specific for LPS will be preferred. The gene encoding the transferase of interest can be either made synthetically or alternatively the gene may be isolated from an appropriate organism either by direct cloning methods or by PCR amplification methods and incorporated into an expression vector. A database suitable for searching of enzymes that may be used to provide for nucleotide precursors such as epimerases, dehydrogenases, transmutases and the like can be found at the following internet address: wit.mcs.anl.gov/WIT2/.

Toxins are often produced by pathogens in precursor form, and in that case it may be the precursor form that can recognise the toxin receptor referred to in this specification.

2. Other Applications

The recombinant microorganism of the invention, and oligosaccharides obtained from the microorganism, are also useful as carriers for oligosaccharides that have a cosmeceutical, diagnostic or pharmacological application. The recombinant microorganisms can, for example, be used to reduce the number of pathogenic organisms from environments such as the oral cavity, the urogenital tract or other mucosal surface, or external environments such as waterways.

Examples of such oligosaccharides and uses that involve modulation of cell adhesion and/or interactions are listed in Table 3.

TABLE 3

| Compound | Possible Mechanism | Use | Reference |
|---|---|---|---|
| Sialyl lactose | | nerve growth factor-like agent for treating aging of nervous system | Japan patent appl. No. 07258093A |
| Sialic acid derivatives (e.g., sialosides from cows milk) | | Hair growth and protection; suppression of dandruff and itchiness | Japan patent appl. no. JP0727929 |
| Sialyl lactose | Inhibits immune complex formation (in vitro) | Rheumatoid arthritis | U.S. Pat. No. 5,614,374 |
| Sialyl lactose (multivalent) | EGF receptor antagonist | Treatment for cancer | WO 97/03701 |
| Sialyl lactose | Reduces inflammation | Psoriasis and acute dermatitis | |
| Sialyl lactose | | Maintain ganglioside content in brain | Japan patent appl. JP09315981 |
| Sialyl lactose | Reduces inflammation (selectin and/or sialoadhesin inhibitor) | Reduction in skin reddening (e.g., cosmetics, sun screens, baby care products, OTC anti-inflammatory agents, acne agents | U.S. Pat. Appl. No. 09/123,251 (pending) |
| Sialyl lactose | Sialoadhesins (inhibition of adhesion) | Immunosuppression (macrophages, granulocytes) sialoadhesin, MAG, CD33, SMP (Swann cell myelin protein) | Crocker et al. (1997) Glycoconjugate J. 14: 601 May et al. (1997) Protein Sci. 6: 717 |

In other applications, the recombinant microorganism of the invention, and oligosaccharides obtained from the microorganism, are useful for gastrointestinal administration Examples of such uses are listed in Table 4.

TABLE 4

| Compound | Possible Mechanism | Use | Reference |
|---|---|---|---|
| Sialyl lactose | | Promotes mineral absorption | |
| Sialyl lactose | Bifidobactor growth promoter | Maintain gut normal flora | Idota et al., Biosci. Biotech. Biochem. 58: 1720 |
| Sialyl lactose | Cholera toxin antagonist | Prevents binding of toxin, reducing diarrhea | Idota et al. (1995) Biosci. Biotech. Biochem. 59: 417 |
| Sialyl lactose | Rotavis adhesion inhibitors | Prevents viral binding, thereby reducing diarrhea | See, e.g., Taiyo Kaguki (1995) J. Agric. Food Chem. 43: 858 |
| Sialyl lactose | Heat-labile E. coli toxin adhesion inhibited | Prevents toxin adhesion, limiting diarrhea | U.S. Pat. No. 5,627,163 |
| Sialyl lactose (and sialic acid derivatives) | Prevents toxin adhesion | Bacterial toxin neutralizer, limiting or preventing diahhrea | U.S. Pat. No. 5,260,380 |
| N-Gc-sialyl lactose | K99 toxin adhesion | Reduces calf scours | Lanne et al. (1995) Biochemistry 34: 1845 Willemsen and DeGraaf (1993) Infect Immun. 61: 4518 |
| Sialyl lactose | Prevents enterotoxigenic E. coli cell adhesion through the CS2 lectin | Reduces incidence of diarrhea | Sjoberg et al. (1988) Biochem J. 255: 105 |
| Sialyl lactose | | Intestinal metabolism improving agent | Japan patent appl. no. JP10029945 |

In other applications, the recombinant microorganism of the invention, and oligosaccharides obtained from the microorganism, are useful for nasopharyngeal administration. Examples of such uses are listed in Table 5.

TABLE 5

| Compound | Possible Mechanism | Use | Reference |
|---|---|---|---|
| Sialyl lactose (a) 2,3 and 2,6 (b) muitivalent | Influenza A and B adhesion | Reduces influenza symptoms by preventing viral adhesion | Frank et al. (1997) J. Mol. Model. 3: 408 Gambaryan et al. (1997) Virology 232: 345 Synthesome, WO 98/14215 Eisen et al. (1997) Virology 237: 19 |
| Sialyl lactose | Paramyxovirus | Treats pig blue eye disease | Reyes-Leyva et al. (1993) Arch. Virol. 133: 195 |
| Sialyl lactose | C. albicans adhesion | Reduces incidence of lung infection | Annaix et al. (1990) FEMS Microbiol. Immun. 64: 147 |
| Sialyl lactose | Polyoma virus adhesion | | Thilo and Harrison (1996) Structure 4: 183 Bauer et al. (1995) J. Virol. 69: 7925 |
| Sialyl lactose | Streptococcus adhesion e.g., pyogenes and mutans e.g., sanguis | Reduces incidence of cavities Reduces incidence of gingivitis | U.S. Pat. No. 5,401,723 Nesser et al. (1995) Glycobiology 5: 97 WO 95/33467 |
| Sialyl LNnT (sialyl lactose) | S. pneumonia adhesion | Reduces otitis media and respiratory tract infections | |
| Sialyl lactose | B. pertussis toxin adhesion | Reduces whooping cough coughing symptoms | |
| Sialyl lactose | | Expectorant | U.S. Pat. No. 4,698,332 |
| Sialyl lactose and | H. influenza | otitis media and | Lock van |

TABLE 5-continued

| Compound | Possible Mechanism | Use | Reference |
|---|---|---|---|
| derivatives (e.g., SLNnT) | adhesion | meningitis | Alphen et al. (1991) Infect. Immun 59: 4473 WO 96/40169 |
| Sialyl lactose (and sialic acid) | Prevents Aspergillus fumigatus binding to lamina and fibrinogen | Reduces infection and severity of infections in diseases such as assinusitis and broncho-putmonary aspergillosis | Bouchara et al. (1997) Infect. and Immun. 65: 2717 |
| Sialyl lactose (multivalent) | Mycoplasma pneumoniae/ hominus adhesion to laminin | Treat or prevent laryngitis and pneumonia, cervical and genital diseases | Krivan, U.S. Pat. No. 5,089,479 Roberts et al. (1989) Biol. Chem. 65: 2717 Tokojenko et al. (1994) Microbiol Zh. 56: 3 |
| Sialyl LNnT | Pneumococcal pneumonia adhesion | Pneumonia | Idanpaan-Heikkila et al. (1997) J. Infect. Dis. 176: 704 WO 95/33467 |
| Sialyl lactose | | Gargle to prevent colds | Japan Patent appl. no. JP90268129 |

The recombinant microorganisms of the invention are also useful to carry bacteriocins. Bacteriocins are described in, for example, WO9506736.

The invention also encompasses a method of testing for the presence of a toxin or a pathogenic microorganism, including the steps of contacting a sample with a recombinant microorganism, or a purified oligosaccharide from a microorganism. Either the carbohydrate or the sample can be immobilised, if desired. Upon binding of the toxin or pathogenic microorganism to the oligosaccharide, the unbound toxin or pathogenic microorganism can be removed by washing. A detection agent is then used to detect bound toxin or pathogenic microorganism.

EXAMPLES

The following examples are offered to illustrate, but not limit the invention.

Example 1

Background

Shiga toxin- (Stx-) producing strains of Escherichia coli (STEC) are important causes of diarrhoea and haemorrhagic colitis (HC) in humans. This can lead to potentially fatal systemic sequelae, such as haemolytic uraemic syndrome (HUS) which is the leading cause of acute renal failure in children (1, 2, 3, 4). Certain other Enterobacteriaceae are also known to produce Stx and cause serious gastrointestinal disease in humans. The most notable of these is Shigella dysenteriae type 1, the causative agent of bacillary dysentery, which is frequently associated with Stx-induced systemic sequelae, including HUS (1). Indeed, it is the principal cause of HUS in parts of Africa and Asia (4). Stx-producing Citrobacter freundii has also been shown to cause diarrhea and HUS in humans, including one outbreak in a German child-care centre (4).

The mortality rate for HUS is 5–10%; other acute complications include stroke, diabetes mellitus, and necrotising colitis necessitating colectomy. The Center for Disease Control and Prevention (Atlanta, Ga.) has estimated that the annual cost for acute care of patients with STEC disease in the USA is in the range of $1–2 billion, with approximately 500 deaths each year (3). In addition, up to a third of survivors sustain permanent renal impairment and may eventually require transplantation (2). Estimates of the on-going cost of management of these long-term complications are not available.

STEC are commonly found in the intestines of livestock, and human infections usually result from consumption of contaminated meat or dairy products; fruit and salad vegetables contaminated with manure, and contaminated drinking or swimming water are also common STEC vehicles. In addition, approximately 20% of all cases of STEC disease are believed to result from person to person transmission (3, 6). STEC belonging to over 100 O:H serotypes have been associated with human disease. However, those belonging to serogroup O157 (particularly O157:H7) are the most prevalent causes of HUS and account for the majority of the major food-bourne outbreaks in the United States, Europe and Britain (2, 3). It is likely, however, that the epidemiological data on the overall incidence of STEC disease and serotype prevalence has been skewed by underdetection of cases caused by non-O157 STEC, which are much more difficult to detect (3, 4). In recent years there have been a number of large outbreaks of STEC disease in North America, the UK, Europe, Japan and Australia Such outbreaks have the potential to overwhelm acute care facilities, even in developed countries with sophisticated health-care systems. The largest (Sakai, Japan, May–June 1996) involved over 8,000 cases of HC (600 requiring hospitalization) and 107 cases of HUS. Another outbreak involving over 500 people and 20 deaths occurred in Scotland in December 1996.

Stx is a compound toxin, consisting of an enzymatically active A subunit (a RNA-N-glycosidase), which inhibits eukaryotic protein synthesis, and a pentameric B subunit responsible for binding to glycolipid receptors in target cell membranes (2). Two major classes of Stx (Stx1 and Stx2) have been distinguished, both by serological methods, as well as by DNA sequence analysis. Individual STEC strains may produce toxins belonging to either or both of the two major Stx classes. However, substantial variation in amino acid sequence occurs within both the Stx1 and Stx2 groups (7, 8, 9, 10,11,12). Within the Stx2 class, several subtypes have been distinguished on the basis of differences in biological properties. All Stx types associated with human disease recognize the same glycolipid receptor, globotriaosyl ceramide ($Gb_3$), which has the structure Galα[1→4]Galβ [1→4]Glc-ceramide (13). Vero (African green monkey kidney) cells express large amounts of $Gb_3$ on their surface, consequently, this cell line is highly susceptible to Stx, and Vero cytotoxicity is the generally recognised standard assay for Stx activity. However, one particular subgroup of Stx2 variants, designated Stx2c, share specific B subunit amino acid differences with respect to classical Stx2 ($Asp_{16}$-Asn and Asp$_{24}$-Ala), which correlate with a somewhat reduced binding affinity for the receptor Gb$_3$ and reduced in vitro cytotoxicity for HeLa cells (14). A separate subgroup, designated Stx2d, is distinguished from other Stx toxins by increased cytotoxicity for Vero cells after incubation in the presence of either mouse proximal small intestinal mucus or human colonic mucus. Activation appears to be a function of the A subunit, because the B subunit is identical to Stx2c, which was not activatable. Activatable Stx2d toxins examined to date share two A subunit amino acid differences with respect to Stx2c (Ser$_{291}$ and Glu$_{297}$), although these alone may not necessarily be sufficient for activation, as they are also found in some Stx2 subtypes which are not activatable (15). A final major Stx2 subtype is Stx2e, which is produced by STEC associated with piglet oedema disease. This is a serious, frequently fatal illness affecting piglets at the time of weaning, and is characterized by neurological symptoms including ataxia, convulsions and paralysis; oedema is typically present in the eyelids, brain, stomach, intestine and mesentery of the colon (16). It is associated with particular STEC serotypes (most commonly O138:K81, O139:K82 and O141:K85, which are not associated with human disease. These particular STEC strains also cause post-weaning diarrhoea in piglets. Stx2e has a different glycolipid receptor specificity from other members of the Stx family, recognising globotetraosyl ceramide (Gb$_4$; GalNAcβ[1→3]Galα[1→4]Galβ[1→4]Glc-ceramide) preferentially over Gb$_3$ (17). Two amino acid differences in the Stx2e B subunit (Gln$_{64}$ and Lys$_{66}$) are critical for this altered specificity, which impacts on the tissue tropism of the toxin, thereby accounting for the distinctive clinical presentation of oedema disease (18).

The pathological features seen in severe human STEC disease (HC and HUS) are directly attributable to the Stx toxins, which are essential for virulence. Pathogenesis of disease initially involves colonization of the gut by the STEC; the bacteria do not invade the gut epithelium, but locally produced Stx is absorbed into the circulation, and the toxin then targets specific tissues in accordance with their Gb$_3$ content. In humans Gb$_3$ is found in highest concentrations in renal tissue, and in microvascular endothelial cells (particularly in the kidneys, gut, pancreas and brain), thereby accounting for the distinct clinical and pathological features of HUS (microangiopathic haemolytic anaemia, thrombocytopoenia and renal failure).

There is increasing evidence that STEC strains vary in their capacity to cause serious disease in humans, and that this, at least in part, is a function of the type and/or amount of Stx produced. Indeed, up to 1000-fold differences in the cytotoxicities of various STEC isolates from humans have been reported. Moreover, patients infected with STEC producing Stx2 are more likely to develop serious complications such as HUS than those infected with STEC producing Stx1 (19,20). The link between Stx2 production and HUS may be a direct consequence of increased in vivo toxicity of Stx2. Indeed, human renal microvascular endothelial cells have been shown to be far more susceptible to the cytotoxic action of Stx2 than Stx1 (21). This is consistent with studies employing a streptomycin-treated mouse model of toxin-induced renal tubular damage. Oral challenge with *E. coli* K-12 carrying cloned Stx2 genes, but not Stx1 genes was capable of inducing fatal tubular damage (22).

The availability of rapid and sensitive methods for diagnosis of STEC infection early in the course of disease has created a window of opportunity for therapeutic intervention. Indeed, during two outbreaks which have occurred in Adelaide we diagnosed STEC infection in patients by PCR almost a week before symptoms of HUS became apparent. The increased awareness that occurs during major outbreaks is likely to result in more patients presenting during the early (diarrhoeal) stage, and when a source of infection has been identified and publicised, persons exposed to the contaminated product may come forward before symptoms appear. An opportunity also exists to treat close contacts of persons with proven or suspected STEC infection (e.g. family members, children in child-care centres, school classmates, etc.), to prevent them from developing serious disease. Antibiotic therapy is contraindicated for STEC infection because of the risk of increasing free Stx in the gut lumen through release of cell-associated toxin and induction of toxin gene expression. There are also concerns that antibiotic therapy might disturb gut flora and result in overgrowth by the STEC. Administration of antimotility agents is also contraindicated (2,4).

During the early stages of human infections, STEC may colonize the gut at high levels (>90% of aerobic flora), exposing the host to sustained high concentrations of Stx and increasing the likelihood of systemic complications. However, as disease progresses, the numbers of STEC decrease markedly, and may even be undetectable in patients who have already progressed to HUS. Western blot analysis using convalescent sera from HUS patients suggests that the elimination of STEC from the gut during the latter stages of HUS is probably a consequence of local immune responses to STEC surface antigens (23). Clearly, in cases of natural STEC infection, the immune response occurs too slowly to prevent Stx-induced complications. Thus, in vivo binding or neutralization of Stx is a potentially important therapeutic strategy. Substances capable of binding Stx in the gut can also play a role as an adjunct to antibiotic therapy.

AU Stx types affecting humans recognise the same glycolipid receptor (Gb$_3$), and at least one strategy exploiting this interaction has been developed. This agent, called Synsorb-Pk, consists of chemically synthesised Galα[1→4]Galβ[1→4]Glc- (the trisaccharide component of Gb$_3$) covalently linked via an 8 carbon spacer to silica particles derived from diatomaceous earth. Synsorb-Pk is capable of binding and neutralizing Stx1 and Stx2 in STEC culture extracts, and in faeces from patients with HC and HUS, although binding of Stx2-related toxins is less efficient than for Stx1 (24,25). 1 mg of Synsorb-Pk has been shown to be capable of binding 93% of a 0.5 ng aliquot of radioiodinated Stx1 (24). Other in vitro studies using purified toxins indicate that the saturation binding capacity of 1 mg of Synsorb-Pk is approximately 5 ng of purified Stx1 or Stx2 (26). In this latter study coincubation experiments indicated that 1 mg of Synsorb-Pk could protect 50% of cells in tissue culture from 2 ng of Stx1 or 0.4 ng of Stx2. A phase I clinical trial did not detect any adverse effects associated with oral administration, and Synsorb-Pk retained its Stx-binding capacity after passage through the human gastrointestinal tract (27). Results of a randomized, double-blind trial vs placebo in children with STEC diarrhoea indicated that oral administration of approximately 500 mg Synsorb-Pk per kg per day reduced the relative risk of progression to HUS by approximately 40%, but only if administered within 3 days of onset of disease (25).

Materials and Methods, Results and Discussion

In this example, the invention resides in construction of a harmless recombinant microorganism capable of incorporating the trisaccharide Galα[1→4]Galβ[1→4] Glc- into the outer core region of its lipopolysaccharide, such that a mimic of the natural host receptor for the toxin is displayed on the bacterial surface. This recombinant microorganism, either live or killed, is capable of binding all Stx types associated with human disease. This microorganism binds Stx2, Stx2c, and Stx2d toxins as effectively as it does Stx1. This is a very important property, since the Stx2-related toxins have greater toxicity for human renal microvascular endothelial cells than Stx1, and strains producing Stx2 are more frequently associated with HUS than those producing only Stx1, as described above. Moreover, this finding was unexpected, given that the synthetic product Synsorb-Pk has a lower binding affinity for Stx2-related toxins than it has for Stx1 (see above). In addition, the recombinant microorganism is capable of binding the oedema disease-associated toxin Stx2e.

Procedure for Construction of Recombinant Bacteria Expressing the Trisaccharide Galα[1→4]Galβ[1→4 Glc- on their Surface In order to locate a source of bacterial genes encoding biosynthesis of the trisaccharide component of the receptor for Stx, we conducted a search of carbohydrate structure databases. This revealed that Galα[1→4]Galβ[1→4]Glc- is found in the outer core region of the lipooligosaccharides (LOS) of *Neisseria meningitidis* (28) and *N. gonorrhoeae* (29), as well as in the LOS of certain strains of *Haemophilus influenzae* (30). LOS are the major glycolipids expressed on the surface of these bacteria, and are analogous to the LPS of other Gram-negative bacterial genera such as Escherichia and Salmonella. LOS and LPS have many structural features in common. Lipid A is the common hydrophobic moiety, and this forms the outer leaflet of the outer membrane. This is linked to the inner core oligosaccharide, which consists largely of heptose and KDO (3-deoxy-D-manno-oct-2-ulosonic acid). The general structural features of lipid A and the inner core oligosaccharide are highly conserved amongst diverse bacterial species, as they are important for outer membrane stability (31,32). The outer region of the core oligosaccharide comprises hexoses, which are linked to the inner core by a variety of highly specific glycosyl transferases. Thus, this region varies in structure from species to species and even within a given bacterial strain (see below). In Enterobacteriaceae, an antigenic repeat-structure O-polysaccharide is attached to the distal end of the outer core oligosaccharide to form high molecular weight LPS. However, in genera such as Neisseria, this does not occur, resulting in a much lower molecular weight LOS (31,32). Pathogenic species of Neisseria have also been shown to sialylate their LOS, an important virulence trait, as this confers a high degree of resistance to the bactericidal activity of serum (29,31).

Another important property of *N. gonorrhoeae* and *N. meningitidis* is the capacity to undergo phase variation which alters the structure (and hence the antigenicity) of the outer core oligosaccharide, thereby avoiding host immune responses. In both species, one of the alternative LOS immunotypes has an outer core consisting of Galα[1→4] Galβ[1→4]Glc-→(referred to as immunotype L1). Phase variation occurs spontaneously and at such high frequency that in any given culture, cells expressing LOS with different outer core oligosaccharide immunotypes will be present. This, as well as the fact that they are pathogens, precludes use of these Neisseria sp. as in vivo toxin-binding agents. Genetic characterization of the region of the *N. gonorrhoeae* chromosome encoding outer core biosynthesis has provided a molecular explanation for the LOS phase variation phenomenon (33,34). This region contains five glycosyl transferase genes, lgtA, lgtB, lgtC, lgtD and lgtE, arranged as an operon. Three of these genes (lgtA, lgtC and lgtD) contain poly-G tracts within the respective open reading frame, which renders them highly susceptible to slipped strand mispairing during replication. Such slippage results in frame shift mutations and concomitant premature termination of translation of the respective specific glycosyl transferase (34). Thus, the actual outer core oligosaccharide structure, and hence immunotype, will depend on which of the lgt genes are encoding functional enzymes at a given point in time. The exact specificity of the five gonococcal glycosyl transferases has been determined by mutational analysis (34). From this we have deduced that expression of the L1 immunotype LOS requires functional lgtE and lgtC genes, which encode the transferases responsible for linking the α-galactosyl and β-galactosyl residues onto the glucose residue attached to the distal end of the inner core oligosaccharide. For this to happen in Neisseria, lgtA must be non-functional, as this gene encodes a highly active N-acetylglucosamine transferase which adds GlcNAc to the outer core in lieu of the terminal α-Gal. The products of lgtB and lgtD, on the other hand, do not appear to interfere with synthesis of immunotype L1, presumably because these transferases have absolute specificity for acceptor oligosaccharides containing GlcNAc (34).

Sequence data for the entire Igt region from both *N. gonorrhoeae* and *N. meningitidis* are available on the GenBank database (accession numbers U14554 and U65788, respectively). This was used to design the oligonucleotide primers shown in Table 6 to direct amplification of lgtC and IgtE genes:

TABLE 6

Primers used for amplification of IgtC and IgtE genes

| Primer | Sequence (5'-3') | Restriction site inserted (underlined) | |
|---|---|---|---|
| LGTCF | GAACAG<u>GAATTC</u>GGCAAGATTATTGTGCC | EcoRI | (SEQ ID. NO:1) |
| LGTCR | TACGTC<u>GGATCC</u>CGTCTGAAGGCTTCAGAC | BamHI | (SEQ ID. NO:2) |

TABLE 6-continued Primers used for amplification of lgtC and lgtE genes

| Primer | Sequence (5'-3') | Restriction site inserted (underlined) | |
|---|---|---|---|
| LGTEF | GCCCTT<u>GGATCC</u>ACCGCAGCTATTGAAACC | BamHI | (SEQ ID NO:3) |
| LGTER | CCATTT<u>AAGCTT</u>TTAATCCCCTATATTTTACAC | HindIII | (SEQ ID NO:4) |

The lgtC and lgtE genes were PCR amplified using primer pairs LGTCF/LGTCR and LGTEF/LGTER, respectively, with *N. Meningitidis* and *N. gonorrhoeae* DNA as template, respectively (the lgtC and lgtE genes from the two species are approximately 95% identical). These PCR products were cloned into the vector pK184 (35) after digestion of both vector and PCR product with EcoRl/BamHI or BamHI/HindIII, respectively, and transformed into *E. coli* K-12. Since the lgtC gene is one of those with a poly-G tract, it was necessary to mutate this region to stabilize expression of the encoded transferase. The DNA sequence of *N. meningitidis* lgtC from nt 157–171 of the open reading frame is CGGGGGGGGGGGGGT (SEQ ID NO:5), which encodes the amino acid sequence Arg-Gly-Gly-Gly-Gly (SEQ ID NO:6). This region of the lgtC gene cloned in pK184 was mutated to CGTGGCGGTGGCGGT (SEQ ID NO:7) by overlap extension PCR. This involved separate PCR amplification of overlapping 5' and 3' portions of the cloned lgtC gene. The 5' portion was amplified using the universal M13 reverse sequencing primer and another with the sequence ATATTACCGCCACCGCCACGCAAATTGGCGGC (SEQ ID NO:8), whereas the 3' portion was amplified using the universal M13 forward sequencing primer and another with the sequence AATTTGCGTGGCGGTGGCGGTAATATCCGCTT (SEQ ID NO:9). The two PCR products were then purified, aliquots were mixed, and full length lgtC with the desired modifications was amplified by PCR using the M13 forward and reverse primers. The PCR product was digested with EcoRI/BamHI and once again cloned into similarly digested pK184, and subjected to sequence analysis to confirm mutagenesis of the poly G tract. This eliminated the possibility of slipped strand mispairing without affecting the amino acid sequence of the encoded protein. The mutated lgtC gene was then excised from the pK184 construct with EcoRI/BamHI and cloned into the compatible restriction sites in the pK184 derivative containing lgtE. This places the lgtC and lgtE genes in tandem in pK184, in the same orientation as the vector lac promoter. The altered lgtC gene sequence take from nt 157–171 of the open reading frame is as follows, the altered nucleotides are shown in bold and underlined TTTGCG<u>T</u>GGC<u>G</u>GT<u>G</u>GC<u>G</u>GTAATAT (SEQ ID NO:10).

The recombinant pK184:lgtCE plasmid was then transformed into a suitable *E. coli* host. In the first instance we used a derivative of *E. coil* R1 (designated CWG308) which has a non-polar insertion mutation in the waaO gene, resulting in expression of an LPS core consisting of just the inner core plus Glc linked to the terminal heptose residue (36). This structure is very similar to the natural substrate for the galactosyl transferase LgtE, and so CWG308 is an appropriate host for expression of lgtCE. A derivative of *E. coli* K-12 with mutations in waaO and waaB is also a suitable host for expression of lgtCE, as it has the same lipopolysaccharide core structure as CWG308. This host has an additional advantage in that it has been proven to be safe for oral administration to humans in very high doses (37). Extensive studies carried out in the early 1980s demonstrated that although it is capable of growth in the human gut, it can not establish long-term, high level colonization, as it lacks adhesins found in pathogenic strains of *E. coli* (37).

Transformation of CWG308 with pK184/lgtCE resulted in synthesis of LPS with an outer core oligosaccharide containing a terminal Galα]1→4]Galβ[1→4]Glc→epitope, as judged by reactivity on dot-immunoblot with a monoclonal antibody specific for the *N. meningitidis* L1 immunotype. Moreover, CWG30b:pK184/lgtCE is capable of directly binding and neutralizing Stx, as detailed below.

Procedure for Testing the Capacity of Recombinant Bacteria to Neutralise Stx

CWG308 and CWG308:pK184/lgtCE were grown overnight at 37° C. in LB broth (supplemented with IPTG and also with 25 µg/ml kanamycin in the case of CWG308:pK184/lgtCE), harvested by centrifugation, washed and resuspended in phosphate-buffered saline (PBS) at a density of approximately $1 \times 10^9$ CFU/ml (equivalent to approximately 2 mg dry weight of cells per ml). In the first instance, French pressure cell (FPC) lysates of fresh overnight LB broth cultures of the following *E. Coli* strains were used as a source of Stx.

TABLE 7

*E. coli* strains used as a source of stx

| Strain | Description | Ref. |
|---|---|---|
| EDL933 | Wild type O157:H7 STEC producing Stx1 and Stx2 | (38) |
| JM109:pJCP521 | *E. coli* JM109 with $Stx_{2c}$ cloned in pBluescript | (11) |
| JM109:pJCP525 | *E. coli* JM109 with $Stx_1$ cloned in pBluescript | (9) |
| JM109:pJCP539 | *E. coli* JM109 with $Stx_2$ cloned in pBluescript | (39) |
| JM109:pJCP542 | *E. coli* JM109 with $Stx_{2d}$ cloned in pBluescript | (8) |
| 128/12 | Wild type piglet oedema disease STEC producing Stx2e | |

FPC lysates of each of the above cultures were filter-sterilized and 0.5 ml aliquots were incubated with 1 ml of CWG308 or CWG308:pK184/lgtCE suspension, or PBS, for 1 hour at 37° C. with gentle agitation. The mixtures were then centrifuged and filter-sterilized. Twelve serial 2-fold dilutions were prepared in tissue culture medium (Dulbecco's Modified Eagles Medium buffered with 20 mM HEPES, and supplemented with 2 mM L-glutamine, 50 IU/ml penicillin and 50 µg/ml streptomycin), commencing at a dilution of 1:20. Fifty µl of each dilution was transferred onto washed Vero cell monolayers in 96well tissue culture trays, and after 30 min incubation at 37° C., a further 150 µl of culture medium was added to each well. Cells were examined microscopically after 72 hours incubation at 37°

C., and scored for cytotoxicity. The endpoint Stx titre was defined as the reciprocal of the highest dilution which still resulted in detectable cytotoxicity. Results for the various Stx extracts are shown below.

TABLE 8

Neutralization of Stx toxins

| | | | | % Stx neutralized by: |
|---|---|---|---|---|
| Stx source | Stx type | Stx titre | CWG308 | CWG308: pK184/lgtCE |
| EDL933 | Stx1 & Stx2 | 40960 | 0 | 99.6 |
| JM109:pJCP521 | Stx2c | 10240 | 0 | 99.8 |
| JM109:pJCP525 | Stx1 | >40960 | 0 | 99.6 |
| JM109:pJCP539 | Stx2 | 10240 | 0 | 98.4 |
| JM109:pJCP542 | Stx2d | 1280 | 0 | >99.2 |
| 128/12 | Stx2e | 1280 | 0 | 87.5 |

The capacity of killed CWG308:pK184/lgtCE cells to bind and neutralize Stx was also examined. Cell suspensions were killed by heating at 65° C. for 3 hours, or by treatment with 1% formaldehyde for 16 hours at 4° C. Capacity to neutralize cytotoxicity in FPC extracts containing Stx1 or StK2c was then compared with that for live CWG308:pK184/lgtCE cells, under the standard conditions described above. The Stx titres for the Stx1 and Stx2c extracts used in this experiment were 40960 in both cases. Heat-killed CWG308:pK184/lgtCE neutralized 93.7% of the Stx1 and 96.8% of the Stx2c. Formaldehyde-killed CWG308:pK184/lgtCE neutralized 99.6% of the Stx1 and 99.2% of the Stx2c. Live CWG308:pK184/lgtCE cells neutralized 99.2% of the Stx1 and 99.6% of the Stx2c. Thus, heat-treatment slightly reduces the capacity of CWG308:pK184/lgtCE cells to bind and neutralize Stx, but formaldehyde-killed CWG308:pK184/lgtCE cells are as effective as live cells. Whilst it is preferable to use live CWG308:pK184/lgtCE from an efficiency point of view because of its capacity to multiply in the gut, thereby increasing the number of cells capable of binding Stx, formaldehyde-killed cells could be used in circumstances where administration of live cells is contraindicated (e.g. immunocompromised patients), or where regulatory approval requirements dictate otherwise.

Presence of both lgtC and lgtE genes in the recombinant plasmid was essential, as CWG308 carrying derivatives of pK184 containing either lgtC or lgtE alone did not bind Stx toxin.

Strains with mutations in genes encoding outer core glycosyl transferases such that a rough LPS comprising the inner core plus Glc linked to the terminal heptose residue is produced can be expected to be preferred hosts for expression of lgtCE. However, it is possible that if expression of these genes in the heterologous host is sufficient, the two encoded galactosyl transferases may compete with endogenous transferases in host strains lacking outer core mutations. This may direct biosynthesis of a modified LPS containing a Stx-binding epitope. This was examined by transforming a range of wild type and mutant *E. coli* and *Salmonella typhimurium* (S enterica sv typhimurium) LT2 strains with pK184/lgtCE and examining the capacity to bind Stx. Experimental conditions were the same as those used for the CWG308 derivative. FPC lysates of *E. coli* JM109:pJCP525 and JM109:pJCP521 were used as a source of STx1 and Stx2c, respectively.

TABLE 9

Neutralization using live receptor mimics

| | % Stx1 neutralized | | % Stx2c neutralized | |
|---|---|---|---|---|
| Strain | −pK184/ lgtCE | +pK184/ lgtCE | −pK184/ lgtCE | +pK184/ lgtCE |
| *E. coli* K-12 C600 | 0 | 99.6 | 0 | 99.2 |
| *E. coli* K-12 D21 | 0 | 99.2 | 0 | 98.4 |
| *E. coli* K-12 D21e7 | 0 | 99.6 | 0 | 93.7 |
| *E. coli* K-12 D21f1 | 0 | 98.4 | 0 | 98.4 |
| *E. coli* B BL21 | 0 | 0 | 0 | 0 |
| *S. typhimurium* LT2 SL3748 | 0 | 99.6 | 0 | 98.4 |
| *S. typhimurium* LT2 SL3750 | 0 | 99.2 | 0 | 96.8 |
| *S. typhimurium* LT2 SL3769 | 0 | 93.7 | 0 | 0 |

All *E. coli* strains are reference to in (64), all Salmonella strains are obtainable from Salmonella Genetic Stock Centre accessible on the internet at the following-address. www.acs.ucalgary.ca/~kesander/index.html Thus, host strains suitable for expression of lgtCE are not limited to strains with mutations in outer core LPS synthesis. Vectors other than pK184 may also be suitable for expression of these genes, including those with higher or lower copy number, different strength promoters (either constitutive or inducible), and those which utilize alternative selection markers, e.g. alternative antibiotic resistance genes, or markers capable of complementing auxotrophic mutations, such as thyA$^+$. Alternatively, the lgtC and lgtE genes could be integrated into the host chromosome by allellic exchange using an appropriate suicide vector such as pCACTUS, or others known to those skilled in the art.

Produce for Measuring Total Stx Binding Capacity of CWG308 pK184/lgtCF

To determine the total binding capacity of CWG308:pK184/lgtCE cells, suspensions containing 5×10$^8$ CFU (1 mg dry weight) in PBS were incubated at 37° C. for 1 hour with aliquots (ranging from 1 ng to 640 μg) of purified Stx1 and Stx2 (obtained from Toxin Technologies Inc., Florida, USA) in a final volume of 0.5 ml, and cytotoxicity was compared with that for similar aliquots of toxin incubated with CWG308.

TABLE 10

Stx binding capacity of recombinant strains

| Amount of Stx | % Stx1 neutralized | % Stx2 neutralized |
|---|---|---|
| 1 ng | 99.98 | 99.95 |
| 5 ng | 99.98 | 99.95 |
| 20 ng | 99.98 | 99.95 |
| 50 ng | 99.95 | 99.9 |
| 100 ng | 99.95 | 99.9 |
| 200 ng | 99.95 | 99.9 |
| 500 ng | 99.2 | 99.9 |
| 1 μg | 99.2 | 99.2 |
| 2 μg | 99.2 | 99.2 |
| 4 μg | 98.4 | 98.4 |
| 8 μg | 98.4 | 96.8 |
| 16 μg | 98.4 | 96.8 |
| 32 μg | 98.4 | 96.8 |

TABLE 10-continued

Stx binding capacity of recombinant strains

| Amount of Stx | % Stx1 neutralized | % Stx2 neutralized |
|---|---|---|
| 40 μg | 98.4 | 96.8 |
| 80 μg | 98.4 | 93.7 |
| 160 μg | 87.5 | 87.5 |
| 320 μg | 50 | 50 |
| 640 μg | 0 | 0 |

From Table 10 it can be seen that the saturation Stx binding capacity of 1 mg of CWG308:pK184/lgtCE cells is approximately 100 μg for both Stx1 and Stx2. This binding capacity is more than 10,000 times greater than that claimed for Synsorb-Pk (25,26).

Procedure for Testing Capacity of Live CWG308:pK184/lgtCE Cells to Protect Mice from Fatal Infection with STEC A streptomycin-treated mouse model of lethal Stx2-induced renal damage has been described previously (12, 22,40). Two wild type STEC strains were used; B2F1 (which produces Stx2d), and 97MW1 (which produces Stx2). B2F1 is known to have very high virulence in this model; mice fed as few as 10 organisms succumb (41). Two groups of 8 streptomycin-treated Balb/C mice were challenged with approximately $1 \times 10^8$ CFU of STEC B2F1; another two groups of 8 mice were challenged with STEC 97MW1. Mice were then given oral doses of approximately $4 \times 10^9$ CFU of either CWG308 or CWG308:pK184/lgtCE suspended in 60 μl of 20% sucrose, 10% NaHCO$_3$, twice per day. The numbers of STEC, as well as-either CWG308 or CWG309:pK184/lgtCE, as appropriate, were monitored in faecal samples from each group. One day (24 hours) after challenge, faecal pellets contained approximately $10^9$ CFU of the respective STEC per g. Faecal pellets from groups which received CWG308:pK184/lgtCE also contained approximately $10^3$ CFU of this strain. For both the B2F1 and 97W1 groups, all of the mice which received oral CWG308 died (median survival time 4 days). However, all of the mice which received CWG308:pK184/lgtCE survived and were alive and well two weeks after challenge. This difference in survival rate (8/8 vs 0/8) is highly significant (P<<0.005, Fisher exact test) and demonstrates unequivocally that oral administration of CWG308:pK184/lgtCE is capable of preventing the fatal systemic complications of STEC disease.

This example has now been published by the inventors in the following journal *Nature Medicine* 6; 265–270 (March 2000).

Example 2

Here we examine the capacity of oral administration of killed recombinant cells to protect mice from otherwise fatal challenge with a highly virulent STEC strain. We have also examined the effect of delaying commencement of therapy on protective efficacy.

Material and Methods

Bacterial strains and plamids.

*E. coli* CWG308 has been described previously (36) and was provided by Chris Whitfield (Department of Microbiology, University of Guelph, Canada). Construction of plasmid pK184/lgtCE (referred to in this example as pJCP-Gb3) is as described in example 1. The Stx2-producing O113:H21 STEC strains 97MW1 and 98NK2 are both clinical isolates from the Women's and Children's Hospital, North Adelaide, South Australia which have been described previously (39). Spontaneous streptomycin-resistant derivatives of these strains used in challenge experiments were isolated by in vitro exposure to the drug. All *E. coli* strains were routinely grown in Luria-Bertani (LB) medium (44) with or without 1.5% Bacto-Agar. Where appropriate streptomycin or kanamycin were added to growth media at a concentration of 50 μg/ml.

Formaldehyde-treatment of *E. coli*.

*E coli* CWG308 or *E. coli* CWG308:pJCP-Gb3 cells were grown overnight in LB broth supplemented with 20 μg/ml IPTG, and 50 μg/ml kanamycin for CWG308:pJCP-Gb3. Cells were harvested by centrifugation, washed and resuspended in PBS at a density of $10^{10}$ CFU/ml (equivalent to 20 mg dry weight of cells per ml). Formaldehyde was added to a final concentration of 1% (vol/vol) and the suspension was held at 4□C for 16 hours. Cells were then washed twice with PBS to remove the formaldehyde and resuspended at the same density in sterile PBS. Complete killing of the *E. coli* suspensions was confirmed by culture. Suspensions were stored at 4° C. for up to two weeks before use.

In vivo protection studies.

The streptomycin-treated mouse model of STEC-induced renal injury has been described previously (Example 1,40, 22). Male 5–6 week old Balb/c mice were given oral streptomycin (5 mg/ml in drinking water) for 24 hours before oral challenge with $1 \times 10^8$ CFU of the streptomycin-resistant STEC. Successful colonisation of each mouse, and maintenance at a level of at least $10^9$ CFU/gm, was confirmed by quantitative culture of faeces on MacConkey agar supplemented with streptomycin. Mice were then given oral doses of approximately 8 mg dry weight of either CWG308 or CWG308:pJCP-Gb3 (formaldehyde-killed) freshly resuspended in 60 μl of 20% sucrose, 10% NaHCO$_3$, twice or three times daily for up to 12 days. Oral streptomycin was continued throughout the experiment. The survival times of mice in each of the groups were recorded. The differences in survival rate between STEC-challenged mice treated with killed CWG308 or CWG308:pJCP-Gb3 were analysed using the Fisher exact test. Kidneys were also removed from selected mice, fixed in formalin and hematoxylin/eosin(HE)-stained sections were examined for histological evidence of renal injury.

Results

In an initial experiment we examined the degree of protection against the highly virulent STEC strain 97MW1 afforded by oral administration of formaldehyde-killed CWG308:pJCP-Gb3. Four groups of six mice were challenged with 97MW1 and then treated with either killed CWG308 or CWG308:pJCP-Gb3. The dose administered (approximately 8 mg dry weight) was the same as that used in example 1 for live bacteria, and this was given either twice daily (ie. every 12 hours, as in our previous study) or three times daily (every 8 hours). FIG. 1 shows that all STEC-challenged mice treated with CWG308 died, with a median survival time of approximately four days. Five of the six mice which were treated with CWG308:pJCP-Gb3 twice daily survived; all six mice which received three doses per day were alive and well at the termination of the experiment.

Figure 2:
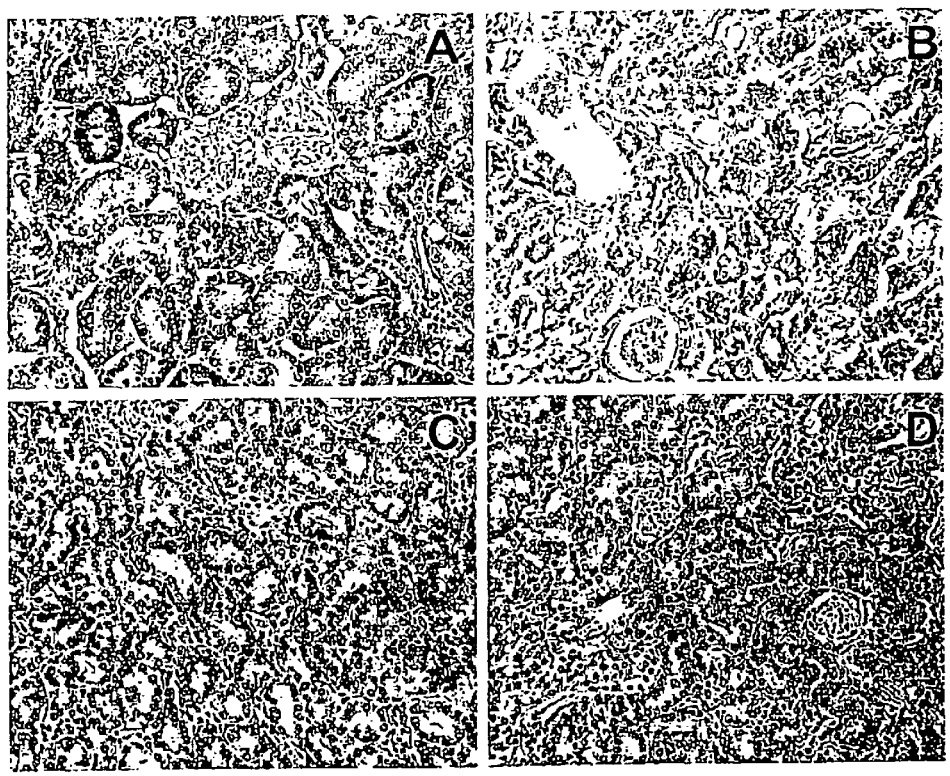

For both of these groups, the survival rate was significantly better than that of the respective control group treated with CWG308 (P<0.005). Histological examination of kidneys removed from CWG308-treated mice revealed extensive Stx-induced tubular necrosis consistent with that seen in previous studies (40,22). In contrast, kidneys removed at the end of the experiment from STEC-challenged mice treated with CWG308:pJCP-Gb3 were indistinguishable from those of unchallenged healthy mice (FIG. 2).

Figure 3:
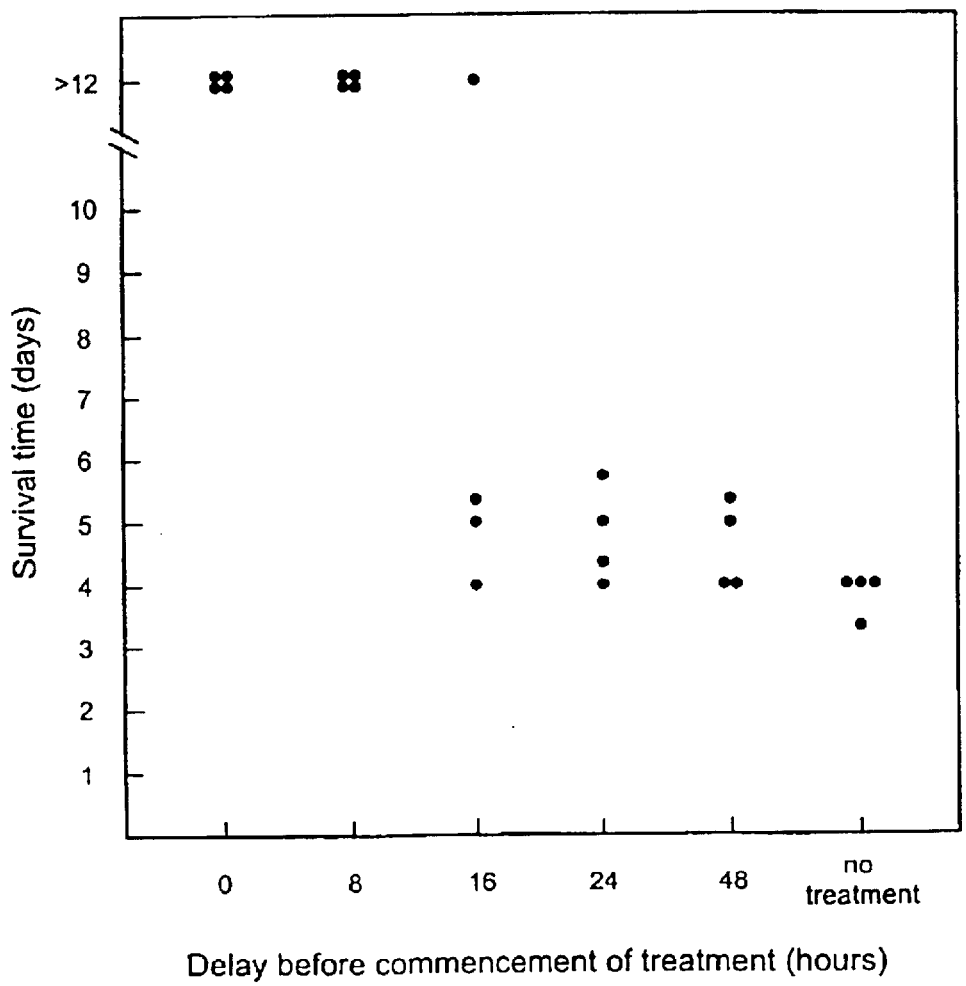
Figure 4:
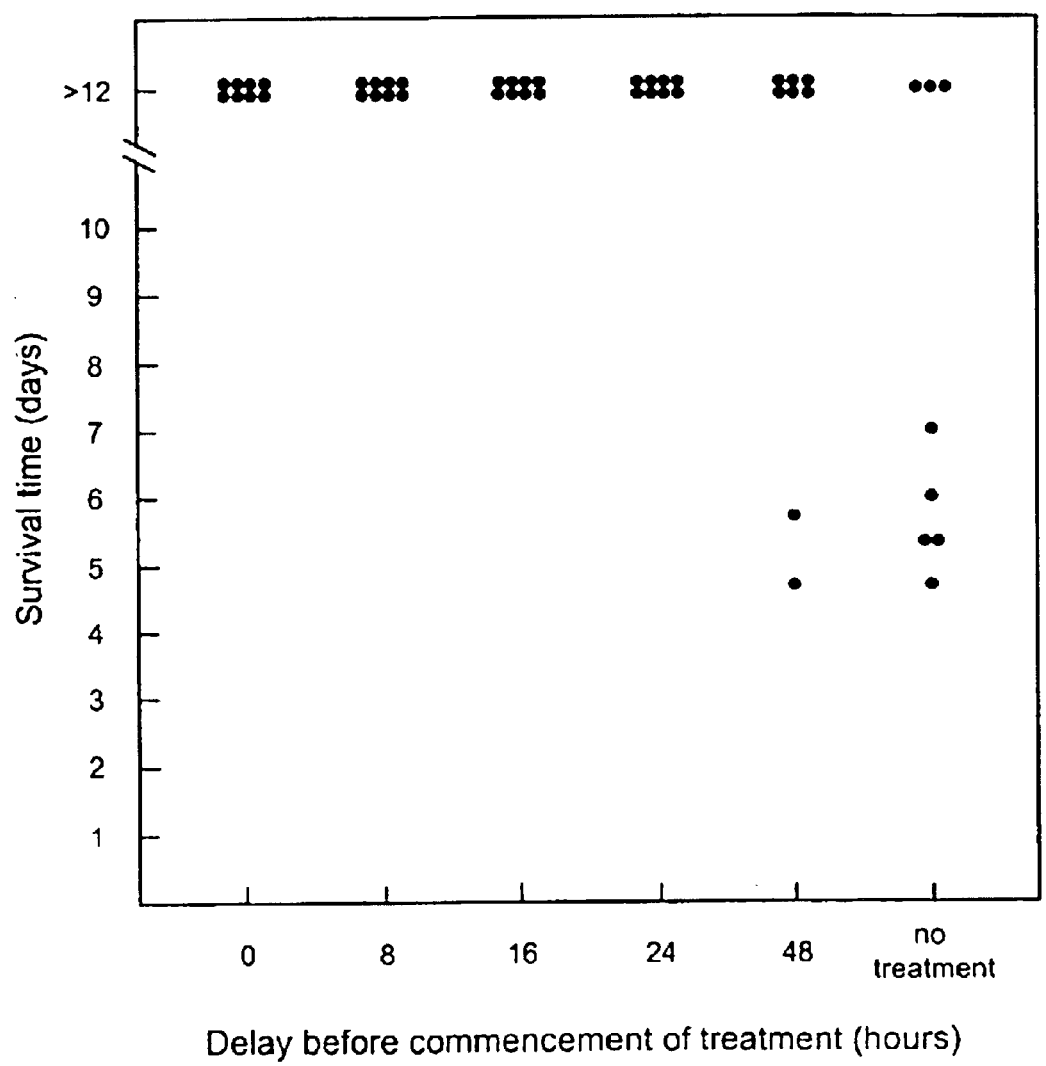

We then investigated the impact of delaying commencement of therapy on survival of STEC-challenged mice. Six groups of four mice were challenged with 97MW1. For five of the groups, therapy with formaldehyde-killed CWG308:pJCP-Gb3 (8 mg dry weight administered 8-hourly) was commenced immediately, or after a delay of 8, 16, 24 or 48 hours; the sixth group did not receive treatment. As shown in FIG. 3, all mice in the untreated group died within four days. All of the mice also died when treatment with CWG308:pJCP-Gb3 was commenced 24 or 48 hours after challenge, although the median survival time was extended slightly. Only one mouse survived when therapy was commenced after 16 hours, but all mice survived when treatment commenced either immediately or eight hours after challenge with 97MW1 (P<0.025, compared with the untreated group). 97MW1 is a highly virulent O113:1H21 STEC strain which grows rapidly in the mouse gut and carries three stx2-related genes (39). Thus, it is capable of releasing large amounts of Stx2 into the gut lumen within hours of infection, and this probably contributes to the rapidly fulminant course of disease. In humans, the lag between acquisition of STEC infection and onset of HUS may be as much as two weeks, and so the above model may underestimate the extent to which commencement of treatment can be delayed. Accordingly, we conducted a similar experiment to that described above using a somewhat less virulent STEC challenge strain, 98NK2. This is also a O113:H21 strain and is closely related to 97MW1, on the basis of pulsed-field gel electrophoretic analysis of genomic DNA, but it carries only one stx2 gene (39). Nevertheless, both strains produce similar levels of Stx in vitro; the titre in culture lysates (determined by Vero cell cytotoxicity assay) was $8.2 \times 10^6$ tissue culture cytotoxic doses per ml. Using 98NK2 as the challenge strain, five of eight untreated mice died, with a median survival time of six days (FIG. 4). In contrast, all eight mice survived in the groups in which treatment with CWG308:pJCP-Gb3 commenced either 0, 8, 16 or 24 hours after challenge (P<0.025). Six of the eight mice also survived when treatment commenced 48 hours after challenge.

Conclusion

The results of this study unequivocally demonstrate that oral administration of formaldehyde-killed recombinant bacteria expressing a mimic of the Stx receptor protects mice from otherwise fatal challenge with a highly virulent STEC strain. The dose of bacteria used was similar to that employed in Example 1. Thus, the capacity to survive in the gut is not an essential feature of this novel therapeutic agent. However, in order to maintain 100% protection, it was necessary to administer formaldehyde-killed cells three times rather than twice daily. The slight reduction in protective efficacy observed with twice daily administration is probably a consequence of clearance of the toxin-binding agent between doses. Estimates of the gut transit time for mice are of the order of eight hours, and so at lower treatment frequencies, mice may be unprotected for the latter portion of each treatment period.

Commencement of therapy immediately after challenge was 100% protective, but in the human setting such early intervention will only be possible for contacts of confirmed cases, who have not yet, or have only just, become infected with STEC. When using the highly virulent challenge strain 97MW1 in our mouse model, delaying commencement of therapy with formaldehyde-killed CWG309:pJCP-Gb3 by 16 or more hours resulted in loss of protection. However, the window of opportunity for treatment was extended to 24–48 hours when a less virulent challenge strain (98NK2) was used. 98NK2 is closely related to 97MW1 and has a similar gut colonisation capacity in the mouse model, as judged by quantitative culture of faeces (result not presented). The principal difference between the two strains is that 97MW1 has three stx2 genes whereas 98NK2 has only one. Nevertheless 98NK2 has high human virulence and was the first LEE-negative STEC strain to be associated with an outbreak of HUS (39). Moreover, 98NK2 is more virulent in the mouse model than most O157:H7 STEC strains.

Although the median survival time of unprotected mice challenged with 98NK2 was six days, compared with only four days for those challenged with 97MW1, this still represents a significant time compression relative to the kinetics of human disease. In the mouse model, streptomycin treatment eliminates endogenous gut flora prior to challenge, and the STEC do not have to compete with other organisms. Under these circumstances, the numbers of STEC in the gut increase very rapidly to $10^9$ to $10^{10}$ CFU per g faeces. Thus, the host is exposed to very high levels of Stx in the lumen almost from the outset, and presumably an ultimately lethal dose is absorbed into the circulation relatively early in the course of infection. In human disease, ingested doses of STEC are usually very low and the pathogen must establish colonisation in competition with endogenous flora. Thus, the time lag between actual infection and onset of systemic complications such as HUS is probably of the order of two weeks. In view of these considerations, it seems probable that a significantly broader window will exist for treatment of human infections. This is supported by the preliminary findings of a phase II clinical trial of a synthetic Stx-binding agent Synsorb-Pk for the prevention of progression of STEC disease in children from diarrhea to HUS. Treatment was associated with a 40% reduction in progression if commenced within three days of onset of gastrointestinal symptoms (45). However, the number of patients was small and a statistically significant difference between treatment and placebo groups was not demonstrable. The practical difficulties of conducting such efficacy trials are considerable, particularly given the low incidence of sporadic STEC cases and the unpredictability of outbreaks. The need to target patients in the early stage of illness is also complicated by the inevitable delays associated with laboratory confirmation of STEC infection; retrospective exclusion of patients whose stool samples ultimately prove to be negative for STEC can upset randomization.

In Example 1 we demonstrated that the in vitro Stx-binding capacity of CWG308:pJCP-Gb3 was 10,000 times better than that reported by others for Synsorb-Pk (24,26). For this reason, we would anticipate improved in vivo performance in humans relative to Synsorb-Pk, although this can only be determined in a large scale clinical trial. Another important consideration is that the Stx-binding microorganism is likely to be extremely cheap to produce on a large scale, and the formaldehyde treatment should preserve it such that it has a long shelf life, particularly in dried form. Low cost and long shelf life will permit presumptive treatment of persons with suspected STEC disease, pending the results of laboratory analysis of faecal samples. This is an important consideration, since the findings of this study indicate that early commencement of therapy will be essential to prevent progression of disease to life-threatening systemic complications.

Example 3
Neutralization of Shiga Toxins Stx1, Stx2c and Stx2e by Recombinant Bacteria Expressing Mimics of Globotriose and Globotetraose The construct of example 1, was somewhat less effective at neutralizing the variant toxin Stx2e produced by STEC strains associated with piglet oedema disease This was not unexpected since Stx2e has been reported to have a different receptor specificity, recognising globotetraosyl ceramide (Gb$_4$; GalNAcβ[1→3]Galα[1→4]Galβ[1→4]Glc-ceramide) preferentially over Gb$_3$ (17). Piglet oedema disease is a serious, frequently fatal STEC-related illness characterized by neurological symptoms including ataxia, convulsions and paralysis; oedema is typically present in the eyelids, brain, stomach, intestine and mesentery of the colon. It is caused by particular STEC serotypes (most commonly O138:K81,O139:K82 and O141:K85), which are not associated with human disease (16,46). The altered glycolipid receptor specificity affects the tissue tropism of the toxin accounting for the distinctive clinical presentation of oedema disease. Oedema disease occurs principally at the time of weaning and so incorporation of an effective Stx2e binding agent into the feed should be capable of preventing disease outbreaks and the associated economic losses. In this example we have constructed a recombinant microorganism expressing globotetraose on its surface and examined its capacity to bind and neutralize Stx2e in vitro.

Construction of an E. coli CWG308 Derivative Expressing GalNAcβ[1→3]Galα[1→4]Galβ[1→4]Glc Globotetraose differs from globotriose only by the additional N-acetylgalactosamine (GalNAc) linked (1→3) to the terminal galactose (Gal). Thus, insertion of a gene encoding the appropriate GalNAc transferase into pJCP-Gb$_3$ would be expected to direct globotetraose expression when introduced into CWG308. The Neisseria lgt locus includes such a gene (lgtD), but this contains a poly-G tract and so is unstable because of susceptibility to slipped strand mispairing (33, 34). To overcome this we mutagenized the lgtD gene by overlap extension PCR using N. gonorrhoeae chromosomal DNA as template. The 5' portion of lgtD was amplified using primers 5'-CAGACG GGATCCGACGTATCGGAAAAGGAGAAAC-3' (LGTDF) (SEQ ID NO:11) incorporating a BamHI site and 5'-GCGCGCAATATATTCACCGCCACCCGACTTTGCC-3' (LGTDOLR) (SEQ ID NO:12). The 3' portion of lgtD was amplified using primers 5'-GGCAAAGTCGGGTGGCGGTGAATATATTGCG CGC-3' (LGTDOLF) (SEQ ID NO:13) and 5'-CATGAT GGATCCTGTTCGGTTTCAATAGC-3' (LGTDR) (SEQ ID NO:14) also incorporating a BamHI site. PCR was performed using the Expand™ High Fidelity PCR System (Roche Molecular Biochemicals) under conditions recommended by the supplier. The two PCR products were then purified, aliquots were mixed, and the complete lgtD coding sequence with the desired modifications was amplified using primers LGTDF and LGTDR. This procedure mutates GGG codons in the poly-G tract to GGT or GGC (all of which encode Gly), eliminating the risk of slipped-strand mispairing without changing the encoded amino acid sequence. The modified PCR product was then digested with BamHI and cloned into similarly digested pJCP-Gb$_3$ between lgtC and lgtE and transformed into E. coli JM109 (47). Insertion of lgtD with the correct mutations and the appropriate orientation was confirmed by sequence analysis of plasmid DNA using custom made oligonucleotide primers and dye-terminator chemistry on an ABI model 377 automated DNA sequencer. That part of the lgtD gene sequence that has been altered is shown below, the sequence shown is taken from nucleotide 3576 to 3586 of genbank accession number U14554, altered nucleotides are shown in bold and underlined. GGG<u>T</u>GG<u>C</u>GG<u>T</u>G (SEQ ID NO:15). This plasmid (designated pJCP-IgtCDE) was then transformed into E. coli CWG308.

Figure 5:
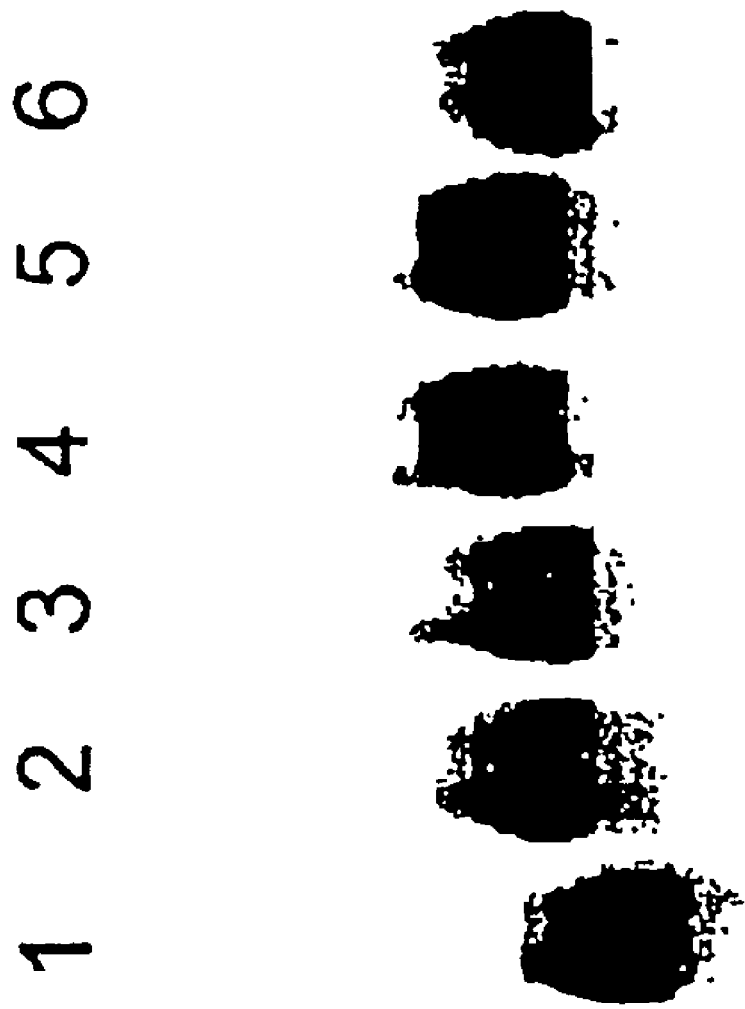

LPS was then purified from the above strain as well as from E. coli CWG308 and CWG308:pJCP-Gb3 and analysed by SDS-polyacrylamide gel electrophoresis with silver-staining as previously described (64). Whilst there was a clear difference in mobility of the LPS from CWG308 and CWG308:pJCP-Gb3, expression of the additional transferase gene in CWG308:pJCP-IgtCDE did not further retard LPS mobility (FIG. 5). This could be explained either by failure to produce functional LgtD or by absence of the essential precursor UDP-GalNAc. This would require a functional UDP-GalNAc-4-epimerase, an enzyme not necessarily present in all E. coli strains. In a previous study (49) we described the genetic locus for biosynthesis of E. coli O113 O-antigen, the repeat unit structure of which includes GalNAc. This locus contains two genes (designated gne and wbnF) encoding proteins with similarity to nucleotide sugar epimerases and we postulated that one or other of these may be a functional UDP-GalNAc-4-epimerase. We therefore amplified the gne and wbnF genes from E. coli O113 chromosomal DNA using primers 5'-TTTATT AAGCTTCCAATTAAGG AGGTAACTC-3' (SEQ ID NO:16) and 5'-AATTACAAGCTTATAATTTTAATTACCA TACCC-3' (SEQ ID NO:17) for gne and primers 5'-ATATTC AAGCTTGAGTGAGGAT TATAAATGAAATT-3' (SEQ ID NO:17) and 5'-TTTCTTAAGCTTTTGTAAAATCAAA CTTTATAGAAG-3' (SEQ ID NO:18) for wbnF (each primer incorporates a HindIII site). Each PCR product was purified, digested with HindIII and ligated with HindIII-digested pJCP-lgtCDE and then transformed into E. coli JM109. Correct insertion and orientation of each construct (designated pJCP-lgtCDE/gne and pJCP-lgtCDE/wbnF) was confirmed by sequence analysis, and then each plasmid was transformed into CWG308. Comparison of the electrophoretic mobility of LPS purified from these recombinant strains (FIG. 5) indicated that expression of the gne gene resulted in an increase in molecular size of the LPS. This gene was originally designated galE (15) because it encoded a product with a high degree of similarity to putative GalE proteins (UDP-Glc4-epimerases) from a large number of bacteria, the most closely related being that from *Yersinia enterocolitica* O:8 (57% identity, 73% similarity) (23). However, the Yersinia galE gene is now designated gne on the Bacterial Polysaccharide Gene Database (available at microbio.usyd.edu.au/BPGD/default.htm) and the function of its product is listed as a UDP-GalNAc-4-epimerase. Given the high degree of similarity between the Yersinia and *E. coli* O113 proteins, and the fact that LgtD is a proven GalNAc transferase (33), we conclude that galE from the *E. coli* O113 rfb locus also encodes a functional UDP-GalNAc-4epimerase, and accordingly it has been renamed gne.

Adsorption/neutralization of Stx

The capacity of the above CWG308 derivatives to adsorb and neutralize various Stx types was then assessed. Filter-sterilized French pressure cell (FPC) lysates of *E. coli* JM109:pJCP522 (13) and JM109:pJCP521 (11) were used as a source of Stx1 and Stx2c, respectively. For Stx2e, we first PCR-amplified the complete stx2e operon from chromosomal DNA extracted from an O141 STEC strain isolated from a piglet with oedema disease. The primers used were 5'-GCATCATGCGTTGTTAGCTC-3' (SEQ ID NO:19) and 5'-AAAGACGCGCATAAATAAACCG-3' (SEQ ID NO:20). The PCR product was purified and blunt-cloned into SmaI-digested pBluescript-SK (Stratagene, La Joll, Calif.) and then transformed into *E. coli* JM109. The insert of this plasmid (designated pJCP543) was sequenced and found to be identical to that previously published for six2e (50), except for a single nucleotide substitution in the A subunit coding region which did not affect the amino acid sequence. Accordingly, a FPC lysate of JM109:pJCP543 was used as a source of Stx2e. The crude Stx extracts were prepared by growing the various *E. coli* JM109 derivatives in 10 ml Luria Bertani (LB) broth supplemented with 50 µg/ml ampicillin overnight at 37° C. Cells were harvested by centrifugation and resuspended in 10 ml phosphate-buffered saline, pH 7.2 (PBS), and lysed in a French pressure cell (FPC) operated at 12,000 p.s.i. Lysates were then sterilized by passage through a 0.45 µm filter.

*E. coli* CWG308, CWG308:pJCP-Gb$_3$, CWG308:pJCP-lgtCDE, CWG308:pJCP-lgtCDE/gne and CWG308:pJCP-lgtCDE/wbnF were then grown overnight in LB supplemented with 20 µg/ml IPTG and 50 µg/ml kanamycin (except for CWG308). Cells were harvested by centrifugation, washed and resuspended in PBS at a density of $10^9$ CFU/ml. Aliquots (250 µl) of the Stx1, Stx2c, and Stx2e extracts were incubated with 500 µl of each of the above suspensions, or PBS, for 1 hour at 37° C. with gentle agitation. The mixtures were then centrifuged and the supernatants were filter-sterilized. Cytotoxicity of the supernatant fraction was then assayed using Vero (African green monkey kidney) cells, which are highly susceptible to all Stx-related toxins (2). Twelve serial 2-fold dilutions were prepared in tissue culture medium (Dulbecco's Modified Eagles Medium buffered with 20 mM HEPES, and supplemented with 2 mM L-glutamine, 50 IU/ml penicilin and 50 µg/ml streptomycin), commencing at a dilution of 1:1 for Stx2e, or 1:20 for Stx1 or Stx2c. Fifty µl of each dilution was transferred onto washed Vero cell monolayers in 96well tissue culture trays, and after 30 min incubation at 37° C., a further 150 µl of culture medium was added to each well. Cells were examined microscopically after 72 hours incubation at 37° C., and scored for cytotoxicity. The endpoint Stx titre (cytotoxic doses [CD] per ml) was defined as the reciprocal of the highest dilution resulting in cytotoxicity in at least 10% of the cells in a given monolayer. As a permanent record, cell monolayers were then fixed in 3.8% formaldehyde-PBS and stained with crystal violet. The percent of Stx adsorbed/neutralized was calculated using the formula $100-(100 \times CD_{CELLS}/CD_{PBS})$, where $CD_{CELLS}$ is the Stx titre in the extracts incubated with the CWG308 derivatives and $CD_{PBS}$ is the Stx titre in the respective Stx extract treated only with PBS. As shown in Table 1, CWG308 exhibited no neutralization activity, whereas CWG308:pJCP-Gb$_3$ bound 99.9, 99.2 and 98.4% of the cytotoxicity of Stx1, Stx2c and Stx2e, respectively. This is in accordance with our previous findings for this globotriose-expressing construct (Example 1) except for a slightly improved neutralization of Stx2e. In Example 1 we observed 87.5% neutralization using a crude lysate of a wild type STEC isolate from a case of oedema disease as a source of Stx2e, but some of the residual cytotoxicity may have been due to the presence of other toxic substances. Neutralization of the various toxin types was not significantly diminished for CWG308:pJCP-lgtCDE and CWG308:pJCP-lgtCDE/wbnF, which was not surprising given that PAGE analysis indicated that the LPS from both of these strains was indistinguishable from that of CWG308:pJCP-Gb$_3$. However, neutralization of both Stx1 and Stx2c was significantly lower for CWG308:pJCP-lgtCDE/gne, which is consistent with the altered electrophoretic mobility of its LPS. Interestingly, it exhibited the same in vitro neutralization activity against Stx2e as the other constructs (98.4%), in spite of expression of what has hitherto been believed to be the preferred receptor for this toxin type.

Conclusion

In the present study we have modified the globotriose-expressing bacterium CWG308:pJCP-Gb$_3$ (example 1) such that it expresses globotetraose (the preferred receptor for Stx2e) by introducing additional genes encoding a GalNAc transferase (IgtD) and a UDP-GalNAc-4-epimerase (gne). Addition of an extra sugar residue to the outer LPS core required both genes, and was demonstrated by electrophoretic analysis. Furthermore, the fact that the LPS migrated as a single species implied that this reaction proceeds to completion. The globotetraose-expressing bacterium had a reduced capacity to neutralize Stx1 and Stx2c in vitro compared to the globotriose expressing bacterium presumably because the terminal GalNAc residue sterically hinders the interaction between the Stx B subunit and the (now subterminal) globotriose moiety. However, its capacity to bind Stx2e was similar to that of the globotriose-expressing construct; both neutralized 98.4% of the cytotoxicity in lysates of *E. coli* JM109 expressing cloned sx$_{2e}$. It has long been held that the piglet oedema disease-associated toxin Stx2e has a higher affinity for Gb$_4$ than for Gb$_3$ (17,13,51). Thus, the findings of this study were somewhat unexpected. Some of the early studies on Stx receptor specificity involved overlaying glycolipids separated by thin layer chromatography with toxin. However, it has been suggested that the polyisobutylmethacrylate used in these studies (to stabilize the silica gel prior to reaction of the separated lipids with toxin) may have induced conformational changes in the carbohydrate moieties which affected toxin-receptor interactions (52). Receptor specificity was also examined on the basis of susceptibility of cell lines containing varying amounts of $Gb_3$ and $Gb_4$ to the toxin. Interestingly, fatty acyl chain length is known to influence the interaction of $Gb_3$ with Stx1 and Stx2 to differing extents, and so it is possible that factors other than the structure of the oligosaccharide component may have been a compounding factor in the cell culture studies (13). In the present study the globotriose and globotetraose moieties were expressed on an otherwise identical platform comprising the inner core oligosaccharide and the lipid A components of E. coli LPS. Thus, differences in toxin-receptor interactions (or lack thereof) truly reflect the impact of oligosaccharide structure and conformation.

Example 4

*Clostridium difficile*

C. difficile infection is associated with broad spectrum antibiotic therapy and is the commonest cause of infectious diarrhoea and life-threatening pseudomembranous colitis in hospitalized patients. Antibiotic therapy permits overgrowth of the gut by this bacterium, which elaborates two potent cytotoxins (exotoxins A and B). Exotoxin A is enterotoxic and is essential for human virulence; exotoxin B can only damage host tissues after destruction of the epithelial barrier by exotoxin A (53). C. difficile exotoxin A binds to several human glycolipids, all of which contain Galβ[1→4]GlcNAc moiety. Genes encoding transferases capable of assembling this epitope are also found in the Neisseria lgt locus. Expression of lgtABE in E. coli CWG308 was predicted to result in synthesis of a LPS outer core oligosaccharide comprising Galβ[1→4]GlcNAcβ[1→3] Galβ[1→4]Glc→ (lacto-N-neotetraose). The lgtA-B genes were amplified from N. gonorrhoeae DNA by PCR, and the poly-G tract in lgtA was mutagenized by overlap-extension PCR, as follows. The 5' portion of lgtA was amplified using primers 5'-CAGGC<u>GAATTC</u>AAATTATCGGGAGAGTA-3' (LGTAF) (SEQ ID NO:21) incorporating an EcoRI site (underlined) and 5'-ATATTCGCCACCGCCACCGCCCGACTTTGCCAATTCG-3' (LGTAOLR) (SEQ ID NO:22). The 3' portion of lgtA and all of lgtB was amplified using primers 5'-GTCGGGCGGTGGCGGTGGCGAATATATTGCGCGCACCG-3' (LGTAOLF) (SEQ ID NO:23) and 5'-CATCTT<u>GGATCC</u>TTTTATTGGAAAGGCAC-3' (LGTBR) (SEQ ID NO:24) incorporating a BamHI site (underlined). PCR was performed using the Expand™ High Fidelity PCR System (Roche Molecular Biochemicals) under conditions recommended by the supplier. The two PCR products were then purified, aliquots were mixed, and the complete lgtAB coding sequence with the desired modifications was amplified using primers LGTAF and LGTBR. This procedure mutates the four consecutive GGG codons in the poly-G tract in lgtA to GGT or GGC (all of which encode Gly), eliminating the risk of slipped-strand mispairing without changing the encoded amino acid sequence. That part of the lgtA gene sequence that has been altered is shown below, the sequence shown is taken from nucleotide 699 to 715 of GenBank accession number U14554, altered nucleotides are shown in bold and underlined. GGG<u>C</u>GGT<u>GGC</u>GGTGG<u>C</u>G (SEQ ID NO:25). The modified PCR product was then digested with EcoRI and BamHI and cloned into the similarly digested derivative of pK184 containing lgtE described earlier. This places lgtAB between the pK184 vector promoter and lgtE, with all three genes in the same orientation such that they will be co-transcribed. Insertion of lgtAB with the correct mutations and the appropriate orientation was confirmed by sequence analysis of plasmid DNA using custom made oligonucleotide primers and dye-terminator chemistry on an ABI model 377 automated DNA sequencer. This plasmid (designated pJCP-LNT) was then transformed into E. coli CWG308.

LPS was then purified from CWG308 derivatives expressing this construct and analysed by SDS-PAGE (using silver staining). This confirmed that expression of lgtABE (encoded on pJCP-LNT) in E. coli CWG308 resulted in production of a higher molecular weight LPS than either CWG308 or CWG308 carrying pJCP-Gb$_3$. This is consistent with expression of the Galβ[1→4]GlcNAcβ[1→3]Galβ[1→4]Glc→(lacto-N-neotetraose) epitope on the cell surface. Capacity to bind and neutralize exotoxin A can then be assessed using filter-sterilized C. difficile culture supernatant or lysate of E. coli K12 expressing cloned toxin genes or purified toxin A as a source of toxin. Such extracts will be incubated with suspensions of (live or formalin-killed) CWG308:pJCP-LNT (or control constructs) with gentle mixing for 1 h at 37° C. Cells can be removed by centrifugation, and serial 2-fold dilutions of filter-sterilized supernatant will be transferred to Vero cell monolayers (in 96-well trays). Monolayers will be scored for C. difficile cytotoxicity at 24 h and the endpoint titre determined. The endpoint titre (cytotoxic doses [CD] per ml) is defined as the reciprocal of the highest dilution resulting in cytotoxicity (characteristic rounding up of cells) in at least 10% of a given monolayer. As a permanent record, cell monolayers can be fixed in 3.8% formaldehyde-PBS and stained with crystal violet. The percent of toxin neutralized can be calculated using the formula $100-(100 \times CD_{CELLS}/CD_{PBS})$, where $CD_{CELLS}$ is the toxin titre in the extracts incubated with a given CWG308 construct, and $CD_{PBS}$ is the toxin titre in the respective sample treated only with PBS.

Interestingly, in vitro studies indicate that even stronger binding occurs between exotoxin A and the trisaccharide Galα[1→3]Galβ[1→4]GlcNAc→, even though it is not present in humans (54). A strain expressing this epitope can be constructed by incorporating a gene encoding a transferase capable of forming the necessary Galα[1→3]Galβ linkage into pJCP-LNT. Databases will be searched for a source of such a transferase. An alternative source is the capsule locus of *Streptococcus pneumoniae* type 11F, which is known to encode such an enzyme. Candidate transferase genes from this locus can be amplified by PCR and cloned into the lacto-N-neotetraose-encoding construct. Heerze et al, (U.S. Pat. No. 5,635,606) have also demonstrated that several other immobilized oligosaccharides, including the trisaccharide Galα[1→3]Galβ[1→4]Glc- are capable of binding C. difficile toxin A. A strain expressing this latter epitope in its outer core LPS can be constructed by expressing the Galα[1→3]Galβ transferase gene referred to above along with just lgtE in *E. coli* CWG308. These derivatives can be tested for toxin binding in parallel with the above constructs.

Although *C. difficile* toxin A is necessary for virulence, significant tissue damage may also result from the action of toxin B, particularly if adsorption of toxin A is incomplete. The actual human receptor for toxin B has not been characterized, but Heerze et al. (U.S. Pat. No. 6,013,635) disclose that immobilized Glcα[1→6]Glc- (isomaltose) or Glcα[1→6]Glcα[1→6]Glc→(isomaltotriose) bind and neutralize toxin B in vitro. Thus, expression of an appropriate glucosyl transferase gene(s) in CWG308, is predicted to confer the capacity to neutralize this cytotoxin.

Example 5

A Receptor Mimic Construct for Treatment of Traveller's Diarrhoea

Traveller's diarrhoea is caused by infection with enterotoxigenic *E. coli* (ETEC). Heat labile enterotoxin (LT) is a major ETEC virulence factor. It binds principally to the ganglioside $G_{M1}$ (Galβ[1→3]GalNACβ[1→4](NeuAcα[2→3]) Galβ[1→4]Glcβ→ceramide) on the enterocyte surface and induces diarrhoea by stimulating adenylate cyclase activity (55). LT is also capable of binding to a variety of other glycoconjugates, as described by Heerze et al. (U.S. Pat. No. 6,069,137). The principal adhesins of ETEC are a family of pili called colonization factor antigens (CFA) or *coli* surface antigens (CS), and these enable the ETEC to colonize the small intestine, an essential step of the pathogenic process. Several potential oligosaccharide receptors have been identified for CFAs, including asialo $G_{M1}$ (Galβ[1→3]GalNAcβ[1→4]Galβ[1→4]Glcβ→ceramide) as well as several sialic acid containing glycoconjugates (56,57). In addition, the disaccharide GalNAc[1→4]Gal has been shown to be a binding sequence for ETEC that express CS3 pili (58). Thus, administration of appropriate receptor mimic constructs would be expected to neutralize the enterotoxic effects of LT as well as blockade adherence of ETEC to the intestinal epithelium Importantly, LT is structurally and functionally related to cholera toxin (CT) produced by *Vibrio cholerae,* which also binds to $G_{M1}$. Thus, any product developed for neutralization of LT and treatment of traveller's diarrhoea will also be effective against cholera.

GM1 is mimicked by the LPS outer core of several *Campylobacter jejuni* strains including the strain deposited as NCTC 11168. These are known to be capable of binding purified CT in vitro (59). The genome sequence of NCTC 11168 is available at sanger.ac.uk/Projects/C jejuni. Moreover, Linton et al. (60) have identified the LOS-encoding region within this sequence and have functionally characterized one of the genes (wlaN) involved in synthesis of the $G_{M1}$ mimic LOS structure. As with some of the Neisseria lgt genes described previously, wlaN has a poly-G tract which will have to be mutagenized to stabilize expression, as described above for lgtA, lgtC, and lgtD. Sequence data for the *C. jejuni* LOS region will be used to design primers for PCR amplification of the appropriate genes for assembly of the $G_{M1}$ mimic on the outer core LPS of CWG308. Additional CWG308 derivatives expressing the alternative LT-binding oligosaccharide epitopes listed in U.S. Pat. No. 6,069,137 can also be constructed. LPS can be extracted from each construct and analysed by SDS-PAGE as before. CWG308 derivatives can then be tested for binding and neutralization of purified CT and LT using a commercial ELISA assay or by direct blotting using commercially available peroxidase-conjugated CT. Protective capacity of any toxin-binding constructs can also be tested in an infant mouse cholera model.

CWG308 derivatives capable of interfering with adherence of ETEC to epithelial cells can be constructed by deletion of the sialyl transferase gene from the $G_{M1}$-expressing strain. Derivatives expressing alternative oligosaccharide receptor mimics capable of blocking adherence of a pathogen can also be constructed. Where data on the receptor specificity of a given CFA/CS family are not available, attempts can be made to determine this by competitive adherence inhibition assay using a panel of soluble mono-, di- and tri-saccharides. This will enable selection of appropriate transferase genes to direct assembly of the chosen epitope on the CWG308 surface. The various constructs can then be tested for capacity to agglutinate a variety of ETEC strains representing all common CFA/CS families, and for capacity to blockade in vitro adherence of these ETEC strains to HEp-2 and Henle 407 cells.

Example 6

Uropathogenic *E. coli* and Porcine Enterotoxigenic *E. coli*

Two further model systems can be used to demonstrate the utility of recombinant receptor mimic technology for blockade of bacterial adhesion. The first is adherence of uropathogenic *E. coli ;* this is mediated by Pap pili, which are known to target the terminal Galα[1→4]Galβ moiety of $Gb_3$ receptors on the uroepithelium (54). Accordingly it is proposed to test the capacity of our existing CWG308:pJCP-$Gb_3$ construct of Example 1 to agglutinate reference uropathogenic *E. coil* strains as well as *E. coli* K-12 clones expressing cloned pup genes. Capacity to blockade in vitro adherence to $Gb_3$-expressing epithelial cell lines (HeLa or Vero cells) can also be examined using standard tissue culture assays. The second example is adhesion of porcine enterotoxigenic *E. coli* strains which express K88ad fimbriae. These pili are known to be specific for facto-N-neotretraose (43), and so CWG308:pJCP-LNT constructed as described above for use with *C. difficile* is predicted to be capable of binding to K88ad fimbriae.

Example 7

*Entamoeba histolyticum*

*E. histilyticum* is an enteric protozoan parasite which causes nearly 40 million cases of colitis or liver abscess each year, of which about 100,000 are fatal. Pathogenesis involves adherence to colonic mucin and colonic epithelial cells, followed by mucosal invasion and host cytolysis (61). Adherence is mediated by a Gal/GalNAc specific lectin, and inhibition of this lectin activity blocks cytotoxicity. *E. histolyticum* binds monomeric and polymeric GalNAc-BSA conjugates with very high efficiency (61). Thus *E. coli* derivatives expressing GalNAc moieties on their surface are proposed to be used for the treatment and prevention of *E. histolyticum* infections. In the first instance, we can investigate whether the CWG308:$Gb_4$ receptor mimic construct of Example 3 (which has a terminal GalNAc moiety) is capable of blockading the infectivity of *E. histolyticum* trophozoites. This can be assayed in vitro by binding to CHO cells, and by cytopathic effect for Caco-2 cells (61). Binding by constructs expressing additional GalNAc moieties can be examined using constructs expressing additional GalNAc transferase genes.

Example 8

Rotavirus

Although the receptor for human rotavirus is yet to be characterized, that for porcine strains has recently been shown to be the sialated gangliosides NeuGc-GM$_3$ and NeuNAc-GM$_3$. Moreover, similar glycolipids present in human breast milk are believed to be responsible for the protection from rotavirus observed in breast-fed infants.

A sialic acid-containing glycolipid termed lactadhesin has been shown to block interaction of human rotavirus with its receptor (65), and thus sialic acid is proposed to act as a mimic for human rotavirus and may be used for therapeutic purposes.

It will be understood that recombinant microorganisms that form the chimeric carbohydrate receptor mimic can be used in the treatment of disease, so that post onset administration can prevent persistence by providing competition with binding receptors or by inhibiting the binding of toxin. Equally it will be apparent in circumstances such as in the outbreak of an infectious event that individuals at high or moderate risk can have the receptor mimics administered to prevent infection.

It will however also be understood that, especially in commercial or sporting animals, administration of the present invention can be prescribed to prevent the onset of a condition. Thus the onset of scours or oedema disease in weanling pigs can be prevented by addition of the microorganisms, or extracts from the microorganisms that include the oligosaccharide-containing binding moieties, to feed. This can be administered over a continuous period during which the weanling piglets are fed or perhaps at intervals during that period to reduce the severity or frequency of onset.

Example 9

Detection of Pathogenic Organisms and Toxins Produced by Them

Detection methods, particularly immunological methods require sufficient avidity between the interaction between for example the antibody on the one part and the antigen on the other. It has been found that for the detection of at least some toxigenic pathogens that monoclonal antibody reagents have not been sufficiently avid to allow the commercialisation of so called dip stick methods. One of the findings of the present invention is the very high capacity of the receptor mimics to interact with toxins. It is thus probably that the chimeric carbohydrates will not only be useful as means of inhibiting the affects of infection or toxin action but also as reagents for the detection of such infectious agents and toxins.

Thus for example lipopolysaccharide is known as a reagent for coating beads, or plastics trays such as ELISA trays, or suitable support surfaces. Thus chimeric carbohydrates can be partially or wholly purified from the recombinant microorganism of the second aspect of the invention and bonded to the support. The sample is then added, washed and then perhaps a suitable labelled antibody used to detect for the presence of bound toxin.

The following protocol can be used:

LPS-Gb$_3$ is prepared using the method of Darveau and Hancock (48). LPS is alkali treated to improve solubility and adhesion to plastics. LPS is used to coat ELISA trays. Non-specific binding sites are blocked with BSA. Diluted samples containing toxin are added to wells of the tray. After incubation, the wells are washed, then incubated with anti-toxin monoclonal antibody. After incubation, the well are washed, then an enzyme conjugated secondary antibody is added to detected bound anti-toxin antibody. After incubation, the walls are washed, then a colour substrate is added, and developed An ELISA reader is used to quantitate the level of toxin binding. This protocol is more particularly set out in reference (65).

REFERENCES

1. O'Brien & Holmes (1987). *Microbiol Rev* 51:206–20.
2. Karmali (1989). *Clin Microbiol Rev* 2:15–38.
3. Nataro & Kaper (1998). *Clin Microbiol Rev* 11:142–201.
4. Paton & Paton (1998). *Clin. Microbiol. Rev.* 11:450–479.
5. Keusch. (1997) Passive and active immunization against STEC and HUS. 3rd International Symposium and Workshop on Shiga Toxin (Verotoxin)—producing *Escherichia coli* Infections, Baltimore, Md., USA. June 1997.
6. Griffin. (1997) Overview of epidemiology of STEC infections in humans. 3rd International Symposium and Workshop on Shiga Toxin (Verotoxin)—producing *Escherichia coli* Infections, Baltimore, Md., USA. June 1997.
7. Gannon et al. (1990). *J Gen Microbiol.* 136:1125–1135.
8. Ito et al. (1990). *Microb. Pathogen.* 8: 47–60.
9. Paton et al (I1995). *Gene.* 153:71–74.
10. Paton et al. (1992). *Microb. Pathog.* 13:225–236.
11. Paton et al. (1993). *Microb. Pathog.* 15:77–82.
12. Paton et al (1995). *Infect. Immun.* 63:2450–2458.
13. Lingwood (1996). *Trends Microbiol.* 4:147–153.
14. Lindgren et al (1994). *Infect. Immun.* 62:623–631.
15. Melton-Celsa et al. (1996). *Infect. Immun.* 64:1569–1576.
16. Imberechts et al (1992). *Vet. Microbiol.* 31:221–233.
17. DeGrandis et al. (1989). *J. Biol. Chem.* 264:12520–12525.
18. Tyrrell et al (1992). *Proc. Natl. Acad. Sci. U S. A.* 89:524–528.
19. Kleanthous et al. (1990). *Arch. Dis. Child.* 65: 722–727.
20. Ostroff et al. (1989). *J. Infect. Dis.* 160: 994–998.
21. Louise & Obrig (1995). *J. Infect. Dis.* 172:1397–1401
22. Wadolkowski et al. (1990). *Infect. Immun.* 58: 3959–65.
23. Voss et al (1998). *Infect. Immun.* 66:1467–1472.
24. Armstrong et al (991). *J. Infect. Dis.* 164:1160–1167.
25. U.S. Pat. No. 5,849,714.
26. Takeda et al (1999). *Microbiol. Immunol.* 43:331–337.
27. Armstrong et al (1995). *J. Infect. Dis.* 171:1042–1045.
28. Wakarchuk et al. (1998). *Eur. J. Biochem.* 254:626–633.
29. Mandrell & Apicella,. (1993). *Immunobiology* 187:382–402.
30. Risberg et al. (1999). *Eur. J. Biochem.* 261: 171–180.
31. Preston et al. (1996). *Crit. Rev. Microbiol.* 22:139–180.
32. Heinrichs et al. (1998). *Mol. Microbiol.* 30:221–232.
33. Gotschlich. (1994). *J. Exp. Med.* 180:2181–2190.
34. Yang & Gotschlich. (1996). *J. Exp. Med.* 183:323–327.

35. Joblng & Holmes (1990) *Nucleic Acids Res* 18: 5315–5316.
36. Heinrichs (1998). *J. Biol. Chem.* 273:29497–29505.
37. Levine et al. (1983). *J. Infect. Dis.* 148:699–709.
38. O'Brien et al. (1984). *Science* 226:694–696.
39. Paton et al. (1999). *J. Clin. Microbiol.* 37;3357–61.
40. Wadolkowski et al. (1990). *Infect. Immun.* 58:2438–2445.
41. Lindgren et al. (1993). *Infect. Immun.* 61:3832–3842.
42. Klemm et al., (1995). *Appl Environ Microbiol* 61:481–486.
43. Grange et al., (1999). *Infect Immun* 67: 165–172.
44. Maniatis et al., (1982) *Molecular cloning: a laboratory manual,* Cold Spring Harbor co Laboratory, Cold Spring Harbor. N.Y.
45. Armstrong et al., (1999). Clinical trials of Synsorb-Pk in preventing hemolytic-uremic syndrome. In: Kaper O Brien eds *Escherichia coli* O157:H7 and other Shiga Toxin-Producing *E. coli* Strains. American Society for Microbiology, Washington, D.C. 1998:374–84
46. Morris & Sojka (1985). *Escherichia coli* as a pathogen in animals, In Sussman (ed). *The virulence of Escherichia coli*. p. 47–77. Society for General Microbiology, Academic Press, London.
47. Yanisch-Perron (1985). i *Gene* 33:103–119
48. Darveau & Hancock (1983). *J. Bacteriol.* 155:831–838
49. Paton & Paton (1999). *Infect. Immun.* 67:5930–5937
50. Weinstein et al., (1988). *J. Bacteriol.* 170:4223–4230
51. Samuel et al., (1990). *Infect. Immun.* 58:611–618
52. Yiu & Gotschlich (1996). *J. Exp. Med.* 183:323–327
53. Kelly & LaMont (1998) *Annu. Rev. Med.* 49:375–390
54. Karlsson (1998) *Mol Microbiol.* 19:1–11
55. Fishman et al., (1993) *Advances in Lipid Research* 25:165–187
56. Bartus et al., (1985) *J. Clin. Microbiol.* 21:951–954
57. Oro et al., (1990) *FEMS Microb. Lett.* 72:289–292
58. Wenneras et al., (1995) *Infect. Immun.* 63:640–646
59. Moran et al., (1996) *FEMS Immunol. Med. Mircrobiol.* 16:105–115
60. Linton et al., (2000) *Mol Microbiol* 37:501–514
61. Pillae et al., (1999) *Infect Immun* 67:3836–3841
62. Phillips et al, (2000) *J. Biol. Chem.* 275:4747–4758
63. Abu Kwaik et al., (1991) *Molec. Microbiol.* 5:2475–2480
64. Morona et al., (1991) *FEMS Microbiol Letts* 66:279–285
65. Newbury (1999) *Current Medicinal Chemistry* 6;117–127
66. Hone et al., (1988) *Infect. Immun.* 56: 1326–1333.
67. Guo et al., (1997) *Science.* 276:250–3.
68. Somerville et al., (1996). *J Clin Invest.* 97:359–65.
69 Khan et al., (1998) *Mol Microbiol.* 29:571–9.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes. Also, a reference within this specification to a document is not to be taken as an admission that the disclosure therein constitutes common general knowledge in Australia.

What is claimed is:

1. A recombinant bacterium selected from the group of species consisting of *Escherichia coli* and *Salmonella enterica* that displays on its surface a binding moiety that acts as a receptor mimic, the binding moiety being a receptor mimic of a receptor for a toxin of a pathogenic microorganism or an adhesin of a pathogenic microorganism, wherein the binding moiety consists of an oligosaccharide which comprises a sugar residue that is attached to an acceptor moiety by a glycosyltransferase that is encoded by an exogenous nucleic acid which is present in the bacterium, said oligosaccharide forming part of a lipopolysaccharide molecule.

2. The recombinant bacterium of claim 1, wherein the oligosaccharide further comprises at least a second sugar residue that is attached to an acceptor moiety by at least a second glycosyltransferase, the second glycosyltransferase being encoded by a second exogenous nucleic acid which is present in the bacterium.

3. The recombinant bacterium of claim 1, wherein the toxin is an enterotoxin.

4. The recombinant bacterium of claim 1, wherein the toxin is selected from the group consisting of shiga toxins, clostridial toxins, cholera toxins, *E. coli* enterotoxins, and Staphylococcal enterotoxins.

5. The recombinant bacterium of claim 4, wherein the toxin is selected from the group consisting of cholera toxin, *E. coli* heat labile enterotoxin types I and II, and ST toxins.

6. The recombinant bacterium of claim 1, wherein the binding moiety comprises an oligosaccharide selected from the group consisting of Galα[1→4]Galβ[1→4]Glc,
Galα[1→4]Galβ,
GalNAcβ[1→3]Galα[1→4]Galβ[1→4]Glc,
Galβ[1→4]GlcNAc,
Galα[→3]Galβ[1→4]Glc,
Galα[1→3]Galβ[1→4GlcNAc,
Galβ[1→4]GlcNAcβ[1→3]Galβ[1→4]Glc,
Glcα[1→6]Glc,
Glcα[1→6]Glcα[1→6]Glc,
NeuNAc,

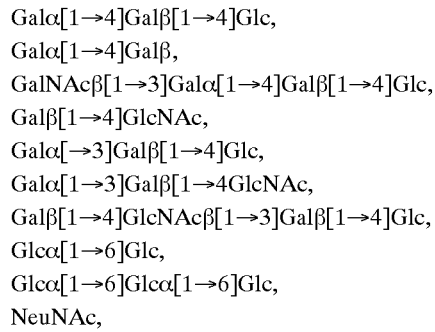

Galβ[1→3]GalNAcβ[1→4]Galβ[1→4]Glc,
GalNAcβ[1→4]Gal,
GalNAc,
Gal,
NeuGc→GM3, and
NeuNAc→GM3.

7. The recombinant bacterium of claim 6, wherein the binding moiety comprises NeuNAc.

8. The recombinant bacterium of claim 6, wherein the binding moiety comprises the oligosaccharide:

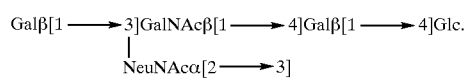

9. The recombinant bacterium of claim 1, wherein the binding moiety is a mimic of a natural receptor for adhesins or toxins produced by a micro-organism selected from a group of genera consisting of Escherichia, Salmonella, Shigella, Citrobacter, Helicobacter, Yersinia, Vibrio, Aeromonas, Campylobacter, Pseudomonas, Pasteurella, Neisseria, Haemophilus, Klebsiella, Staphylococcus, Streptococcus, Clostridium, rotavirus, and Entamoeba.

10. The recombinant bacterium of claim 1, wherein the bacterium further comprises one or more exogenous enzymes involved in synthesis of a nucleotide sugar which serves as a donor for the glycosyltransferase.

11. The recombinant bacterium of claim 10, wherein the nucleotide sugar is selected from the group consisting of GDP-Man, UDP-Glc, UDP-Gal, UDP-GlcNAc, UDP-GalNAc, CMP-sialic acid, GDP-Fuc, and UDP-xylose.

12. The recombinant bacterium of claim 10, wherein the enzyme is a nucleotide sugar synthetase.

13. The recombinant bacterium of claim 10, wherein the enzyme is involved in synthesis of a nucleotide that comprises the nucleotide sugar.

14. The recombinant bacterium of claim 10, wherein the enzyme is involved in synthesis of a sugar that comprises the nucleotide sugar.

15. The recombinant bacterium of claim 10, wherein the one or more sugars transferred to the acceptor molecule by the exogenous glycosyltransferases make up the entirety of the receptor mimic.

16. The recombinant bacterium as in claim 1, wherein a combination of sugars of the acceptor molecule and the one or more sugars transferred to the acceptor molecule by the exogenous glycosyltransferases make up the entirety of the receptor mimic.

17. The recombinant bacterium as in claim 1, wherein the acceptor moiety is all or a portion of the core of the lipopolysaccharide.

18. A pharmaceutical preparation for enteral administration, said preparation comprising a recombinant delivery bacterium and a pharmaceutically acceptable excipient,
 wherein the delivery bacterium is selected from the group of species consisting of *Escherichia coli* and *Salmonella enterica*,
 wherein the delivery bacterium expresses one or more exogenous glycosyltransferases encoded by an exogenous nucleic acid and an acceptor molecule,
 wherein said one or more exogenous glycosyltransferases are specific for the transfer of one or more sugar residues represented progressively from a non reducing terminal end of a receptor of either a toxin of a pathogenic microorganism or an adhesin of a pathogenic microorganism, and further wherein the one or more glycosyltransferases progressively transfer said one or more sugar residues onto the acceptor molecule to thereby form a chimeric carbohydrate molecule with an exposed receptor mimic,
 wherein said exposed receptor mimic is capable of binding the toxin or the adhesin, and further wherein a combination of sugars of the acceptor molecule and the one or more sugars transferred to the acceptor molecule make up the entirety of the receptor mimic,
 and wherein said chimeric carbohydrate molecule is a lipopolysaccharide molecule.

19. The pharmaceutical preparation as in claim 18, wherein the receptor mimic is a mimic of the receptor of a bacterial toxin.

20. The pharmaceutical preparation as in claim 19, wherein the toxin is selected from the group consisting of shiga toxins, clostridial toxins, cholera toxins, *E. coli* enterotoxins, and Staphylococcal enterotoxins.

21. The pharmaceutical preparation as in claim 20, wherein the toxin is a clostridial toxin.

22. The pharmaceutical preparation as in claim 18, wherein the receptor mimic is partially or wholly formed within a sugar moiety selected from the group consisting of:

Galα[1→4]Galβ[1→4]Glc,

Galα[1→4]Galβ,

GalNAcβ[1→3]Galα[1→4]Galβ[1→4]Glc,

Galβ[1→4]GlcNAc,

Galα[1→3]Galβ[1→4]Glc,

Galα[1→3]Galβ[1→4]GlcNAc,

Galβ[1→4]GlcNAcβ[1→3]Galβ[1→4]Glc,

Glcα[1→6]Glc,

Glcα[1→6]Glcα[1→6]Glc,

NeuNAc,

Galβ[1———→3]GalNAcβ[1———→4]Galβ[1———→4]Glc,
 |
 NeuNAcα[2———→3]

Galβ[1→3]GalNAcβ[1→4]Galβ[1→4]Glc,

GalNAcβ[1→4]Gal,

GalNAc,

Gal,

NeuGc→GM3, and

NeuNAc→GM3.

23. The pharmaceutical preparation as in claim 18, wherein one or more exogenous nucleotide sugar precursor synthesizing enzymes encoded by a second exogenous nucleic acid are also expressed by said delivery bacterium, said sugar precursor enzymes forming precursors to make up said chimeric carbohydrate.

24. The pharmaceutical preparation as in claim 18, wherein the delivery bacterium is non harmful and live.

25. The pharmaceutical preparation as in claim 18, wherein the delivery bacterium is protected by a protective capsule or held within a protective matrix.

26. The pharmaceutical preparation as in claim 18, wherein the delivery bacterium is killed before administration of the pharmaceutical preparation.

27. The pharmaceutical preparation as in claim 26, wherein the delivery bacterium is killed by treatment with a chemical agent selected from the group consisting of formalin or thiomersal, or by treatment with a bactericidal antibiotic, or by exposure to heat or UV irradiation.

28. A recombinant *E. coli* that displays on its surface a binding moiety that acts as a receptor mimic when admin istered to an animal, and competes with a ligand for binding to a receptor for the ligand, wherein the receptor mimic consists of an oligosaccharide which comprises a sugar residue that is attached to an acceptor moiety by a glycosyltransferase that is encoded by an exogenous nucleic acid which is present in the *E. coli,* said oligosaccharide forming part of a lipopolysaccharide molecule.

29. The recombinant *E. coli* of claim 28, wherein the oligosaccharide is Galα[1→4]Galβ[1→4]Glc.

30. The recombinant *E. coli* of claim 28, wherein the oligosaccharide is GalNAcβ[1→3]Galα[1→4]Galβ[1→4]Glc.

31. The recombinant bacterium as in claim 1 wherein said bacterium is *Escherichia coli*.

32. The pharmaceutical preparation as in claim 18 wherein said delivery bacterium is *Escherichia coli*.

* * * * *